(12) United States Patent
Liu

(10) Patent No.: US 8,420,775 B2
(45) Date of Patent: Apr. 16, 2013

(54) POLYPEPTIDES AND METHODS FOR MODULATING D1-D2 DOPAMINE RECEPTOR INTERACTION AND FUNCTION

(75) Inventor: Fang Liu, Mississauga (CA)

(73) Assignee: Centre for Addiction and Mental Health, Toronto, Ontario (CA)

( * ) Notice: Subject to any disclaimer, the term of this patent is extended or adjusted under 35 U.S.C. 154(b) by 65 days.

(21) Appl. No.: 12/997,813

(22) PCT Filed: Jun. 12, 2009

(86) PCT No.: PCT/CA2009/000829
§ 371 (c)(1),
(2), (4) Date: Dec. 13, 2010

(87) PCT Pub. No.: WO2009/149560
PCT Pub. Date: Dec. 17, 2009

(65) Prior Publication Data
US 2012/0134991 A1    May 31, 2012

Related U.S. Application Data

(60) Provisional application No. 61/060,948, filed on Jun. 12, 2008.

(51) Int. Cl.
*A61K 38/00* (2006.01)
*A61K 38/04* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)
*C07K 14/575* (2006.01)
*A61P 25/18* (2006.01)
*A61P 25/22* (2006.01)
*A61P 25/24* (2006.01)

(52) U.S. Cl.
USPC ........ 530/300; 514/17.5; 514/17.6; 514/18.1; 530/324; 530/325; 530/326

(58) Field of Classification Search .................. None
See application file for complete search history.

(56) References Cited

U.S. PATENT DOCUMENTS

| | | | |
|---|---|---|---|
| 5,652,122 | A | 7/1997 | Frankel et al. |
| 5,670,617 | A | 9/1997 | Frankel et al. |
| 5,674,980 | A | 10/1997 | Frankel et al. |
| 5,747,641 | A | 5/1998 | Frankel et al. |
| 5,804,604 | A | 9/1998 | Frankel et al. |
| 7,214,496 | B2 | 5/2007 | Oakley et al. |
| 2002/0142299 | A1 | 10/2002 | Davidson et al. |
| 2003/0186890 | A1 | 10/2003 | Drin et al. |
| 2004/0209797 | A1 | 10/2004 | Karas |
| 2008/0234183 | A1 | 9/2008 | Hallbrink et al. |
| 2009/0037118 | A1* | 2/2009 | Abrol et al. ............ 702/20 |

FOREIGN PATENT DOCUMENTS

| | | |
|---|---|---|
| WO | 9907728 A2 | 2/1999 |
| WO | 0115511 A2 | 3/2001 |
| WO | 03106491 A2 | 12/2003 |

OTHER PUBLICATIONS

Written Opinion and International Search Report for PCT/CA2009/000829, The Written Opinion was completed by the Canadian Patent Office on Aug. 27, 2009, The International Search Report was completed by the Canadian Patent Office on Aug. 4, 2009, All together 16 Pages.
Picetti et al. "Dopamine D2 Receptors in Signal Transduction and Behavior", Critical Reviews in Neurobiology 1997, vol. 11, No. 2&3, p. 121-142.
Park et al. "Par-4 Links Dopamine Signaling and Depression", Cell Jul. 29, 2005, vol. 122, p. 275-287.
Canadian Community Health Survey Mental Health and Well-Being 2002, 1 Page.
Dewa et al. "Bridging Academia and Business: Exploring the Workplace Burden of Mental Illness", The Economics of Neuroscience 2000, vol. 2, No. 6, p. 47-49.
Missale et al. "Dopamine Receptors: From Structure to Function", Physiological Reviews Jan. 1998, vol. 78, No. 1, p. 189-225.
Nestler et al. "Neurobiology of Depression", Neuron Mar. 28, 2002, vol. 34, p. 13-25.
Vaidya et al. "Depression—emerging insights from neurobiology", British Medical Bulletin 2001, vol. 57, p. 61-79.
Beninger et al. "Dopamine D1-like Receptors and Reward-related Inventive Learning", Neuroscience & Biobehavioral Reviews 1998, vol. 22, No. 2, p. 335-345.
Hagan et al. "Parkinson's Disease: Prospects for Improved Drug Therapy", Trends Pharmacol Sci May 1997, vol. 18, No. 5, p. 156-163.
Hollerman et al. "Influence of Reward Expectation on Behavior-Related Neuronal Activity in Primate Striatum", J Neurophysiol 1998. vol. 80, p. 947-963.
Iversen. "Interactions between excitatory amino acids and dopamine systems in the forebrain: implications for schizophrenia and Parkinson's disease", Behavioural Pharmacology 1995, vol. 6, p. 478-491.
Schultz. "Dopamine neurons and their role in reward mechanisms", Curr Opin Neurobiol 1997, vol. 7, No. 2, p. 191-197.
Watanabe et al. "Increase of Extracellular Dopamine in Primate Prefrontal Cortex During a Working Memory Tast", J Neurophysiol 1997, vol. 78, p. 2795-2798.

(Continued)

*Primary Examiner* — Robert Landsman
(74) *Attorney, Agent, or Firm* — Brooks Kushman P.C.

(57) ABSTRACT

The present invention provides for prevention and/or treatment of neurological or neuropsychiatric disorders involving abnormal D1-D2 dopamine receptor coupling and/or activation. Methods and agents are provided for modulating dopamine receptor function arising from D1-D2 coupling and/or activation. Agents of the present invention include fragments of D2 receptor or D1 receptor that can disrupt D1-D2 coupling.

8 Claims, 14 Drawing Sheets

OTHER PUBLICATIONS

Tremblay et al. "Probing Brain Reward System Function in Major Depressive Disorder", Arch Gen Psychiatry 2002, vol. 59, No. 5, p. 409-416.
Kapur et al. "Role of the Dopaminergic System in Depression", Biol Psychiatry 1992, vol. 32, No. 1 p. 1-17.
Anisman et al. "Deficits of Escape Performance Following Catecholamine Depletion: Implications for Behavioral Deficits Induced by Uncontrollable Stress", Psychopharmacology 1979, vol. 64, p. 163-170.
Anisman et al. "Effects of Inescapable Shock on Subsequent Escape Performance: Catecholaminergic and Cholinergic Mediation of Response Initiation and Maintenance", Psychopharmacology 1979, vol. 61, p. 107-124.
D'Aquila et al. "The role of dopamine in the mechanism of action of antidepressant drugs", European Journal of Pharmacology 2000, vol. 405, p. 365-373.
Basso et al. "Antidepressant-Like Effect of D2/3 Receptor-, But not D4 Receptor-Activation in the Rat Forced Swim Test", Neuropsychopharmacology 2005, vol. 30, p. 1257-1268.
Cervo et al. "The role of the mesolimbic dopaminergic system in the desipramine effect in the forced swimming test", European Journal of Pharmacology 1990, vol. 178, p. 129-133.
Gambarana et al. "Imipramine and fluoxetine prevent the stress-induced escape deficits in rats through a distinct mechanism of action", Behavioural Pharmacology 1995, vol. 6, p. 66-73.
Hirano et al. "Involvement of dopamine D1 receptors and a1-adrenoceptors in the antidepressant-like effect of chlorpheniramine in the mouse tail suspension test", European Journal of Pharmacology 2007, vol. 562, p. 72-76.
Muscat et al. "Dopaminergic Mechanism of Imipramine Action in an Animal Model of Depression", Biol Psychiatry 1990, vol. 28, p. 223-230.
Nikulina et al. "Role of genotype and dopamine receptors in behaviour of inbred mice in a forced swimming test", Psychopharmacology 1991, vol. 105, p. 525-529.
Renard et al. "Is dopamine implicated in the antidepressant-like effects of selective serotonin reuptake inhibitors in the mouse forced swimming test?", Psychopharmacology 2001, vol. 159, p. 42-50.
Rogoz et al. "Mechanism of synergistic action following co-treatment with pramipexole and fluoxetine or sertraline in the forced swimming test in rats", Pharmacological Reports 2006, vol. 58, p. 493-500.
Sampson et al. "Reversal of antidepressant action by dopamine antagonists in an animal model of depression", Psychopharmacology 1991, vol. 104, p. 491-495.
Vaudeois et al. "Indirect Dopamine Agonists Effects on Despair Test: Dissociation From Hyperactivity", Pharmacology Biochemistry and Behavior 1996, vol. 54, No. 1, p. 235-239.
Wang et al. "Effects of Apomorphine on the Expression of Learned Helplessness Behavior", Chinese Journal of Physiology 2007, vol. 50, No. 2, p. 63-68.
Yamada et al. "Involvement of dopamine receptors in the anti-immobility effects of dopamine re-uptake inhibitors in the forced swimming test", European Journal of Pharmacology 2004, vol. 504, p. 207-211.
Learned-Coughlin et al. "In Vivo Activity of Bupropion at the Human Dopamine Transporter as Measured by Positron Emission Tomography", Biol Psychiatry 2003, vol. 54, No. 8, p. 800-805.
Meyer et al. "Bupropion occupancy of the dopamine transporter is low during clinical treatment", Psychopharmacology 2002, vol. 163, p. 102-105.
Corrigan et al. "Coparison of Pramipexole, Fluoxetine, and Placebo in Patients with Major Depression", Depression and Anxiety 2000, vol. 11, p. 58-65.
Goldberg et al. "Pramipexole in Refractory Bipolar Depression", Am J Psychiatry May 1999, vol. 156, No. 5, p. 798.
Perugi et al. "Adjunctive Dopamine Agonists in Treatment-Resistant Bipolar II Depression: an Open Case Series", Pharmacopsychiatry 2001, vol. 34, No. 4, p. 137-141.
Post et al. "Effects of a Dopamine Agonist Piribedil in Depression Patients", Arch Gen Psychiatry May 1978, vol. 35, No. 5, p. 609-615.
Sitland-Marken et al. "Psychiatric Applications of Bromocriptine Therapy", J Clin Psychiatry Feb. 1990, vol. 51, No. 2, p. 68-82.
D'Haenen et al. "Dopamine D2 Receptors in Depression Measured with Single Photon Emission Computer Tomography", Biol Psychiatry 1994, vol. 35, No. 2, p. 128-132.
Ebert et al. "Dopamine and depression—Striatal dopamine D2 receptor SPECT before and after antidepressant therapy", Psychopharmacology 1996, vol. 126, p. 91-94.
Klimke et al. "Dopamine D2 receptor binding before and after treatment of major depression measured by [123I]IBZM SPECT", Psychiatry Research: Neuroimaging Section 1999, vol. 90, p. 91-101.
Parsey et al. "Dopamine D2 Receptor Availability and Amphetamine-Induced Dopamine Release in Unipolar Depression", Biol Psychiatry 2001, vol. 50, No. 5, p. 313-322.
Shah et al. "Clinical and psychometric correlates of dopamine D2 binding in depression", Psychological Medicine 1997, vol. 27, p. 1247-1256.
Marinelli et al. "Review Article: Interaction between glucocorticoid hormones, stress and psychostimulant drugs", European Journal of Neuroscience 2002, vol. 16, p. 387-394.
Oswald et al. "Relationships Among Ventral Striatal Dopamine Release, Cortisol Secretion, and Subjective Responses to Amphetamine", Neuropsychopharmacology 2005, vol. 30, p. 821-832.
Gerson et al. "Minireview: Motor Effects of Serotonin in the Central Nervous System", Life Siences 1980, vol. 27, p. 1435-1451.
Prisco et al. "Serotonin-Dopamine Interaction in the Rat Ventral Tegmental Area: An Electrophysiological Study in Vivo", The Journal of Pharmacology and Experimental Therapeutics 1994, vol. 271, No. 1, p. 83-90.
Andreasen. "Linking Mind and Brain in the Study of Mental Illnesses: A Project for a Scientific Psychopathology", Science 1997, vol. 275, p. 1587-1593.
Flaum et al. "The Core Symptoms of Schizophrenia", Annals of Medicine 1996, vol. 28, p. 525-531.
Hietale et al. "Dopamine in Schizophrenia", Annals of Medicine 1996, vol. 28, p. 557-561.
Seeman et al. "Antipsychotic Drugs: Direct Correlation between Clinical Potency and Presynaptic Action on Dopamine Neurons", Science 1975, vol. 188, p. 1217-1219.
Creese et al. "Dopamine Receptor Binding Predicts Clinical and Pharmacological Potencies of Antischizophrenic Drugs", Science 1976, vol. 192, p. 481-483.
Kapur et al. "Half a century of antipsychotics and still a central role for dopamine D2 receptors", Progress in Neuro-Psychopharmacology & Biological Psychiatry 2003, vol. 27, p. 1081-1090.
Davis et al. "Dopamine in Schizophrenia: A Reviews and Reconceptualization", Am J Psychiatry Nov. 1991, vol. 148, p. 1474-1486.
Weinberger et al. "Mesocortical Dopaminergic Function and Human Cognition", Ann NY Acad Sci 1988, vol. 537, p. 330-338.
Laruelle et al. "Glutamate, Dopamine, and Schizophrenia From Pathophysiology to Treatment", Ann NY Acad Sci 2003, vol. 1003, p. 138-158.
Knable et al. "Dopamine, the prefrontal cortex and schizophrenia", Journal of Psychopharmacology 1997, vol. 11, No. 2, p. 123-131.
Hall et al. "Distribution of D1- and D2-Dopamine Receptors, and Dopamine and Its Metabolites in the Human Brain", Neuropsychopharmacology 1994, vol. 11, No. 4, p. 245-256.
Lidow et al. "Distribution of Dopaminergic Receptors in the Primate Cerebral Cortex: Quantitative Autoradiographic Analysis Using [3H]Raclopride, [3H]Spiperone and [3H]SCH23390", Neuroscience 1991, vol. 40, No. 3, p. 657-671.
Okudo et al. "Decreased prefrontal dopamine D1 receptors in schizophrenia revealed by PET", Nature Feb. 1997, vol. 385, p. 634-636.
Abi-Dargham et al. "Prefrontal Dopamine D1 Receptors and Working Memory is Schizophrenia", The Journal of Neuroscience May 1, 2002, vol. 22, No. 9, p. 3708-3719.
Williams et al. "Modulation of memory fields by dopamine D1 receptors in prefrontal cortex", Nature Aug. 1995, vol. 376, p. 572-575.
Goldman-Rakic et al. "D1 Receptors in Prefrontal Cells and Circuits", Brain Research Interactive 2000, vol. 31, p. 295-301.

Castner et al. "Reversal of Antipsychotic-Induced Working Memory Deficits by Short-Term Dopamine D1 Receptor Stimulation", Science Mar. 17, 2000, vol. 287, No. 5460, p. 2020-2022.

Davidson et al. "Effects of D-1 Agonist SKF-38393 Combined with Haloperidol in Schizophrenic Patients", Arch Gen Psychiatry Feb. 1990, vol. 47, p. 190-191.

Muler et al. "D1—Versus D2-Receptor Modulation of Visuospatial Working Memory in Humans", The Journal of Neuroscience Apr. 1, 1998, vol. 18, No. 7, p. 2720-2728.

Seeman et al. "Link between D1 and D2 dopamine receptors is reduced in schizophrenia and Huntington diseased brain", Proc Natl Acad Sci Dec. 1989, vol. 86, p. 10156-10160.

Calabresi et al. "Coativation of D1 and D2 dopamine receptors is required for long-term synaptic depression in the striatum", Neuroscience Letters 1992, vol. 142, p. 95-99.

Castellano et al. "The effects of anandamide on memory consolidation in mice involve both D1 and D2 dopamine receptors", Behavioral Pharmacology 1997, vol. 8, p. 707-712.

Gerfen et al. "D1 and D2 dopamine receptor function in the striatum: Coactivation of D1- and D2-dopamine receptors on separate populations of neurons results in potentiated immediate early gene response in D1-containing neurons", The Journal of Neuroscience Dec. 1995, vol. 15, No. 12, p. 8167-8176.

Hyman et al. "Neural Mechanisms of Addiction: The role of Reward-Related Learning and Memory", The Annual Review of Neuroscience 2006, vol. 29, p. 565-598.

Keefe et al. "D1-D2 Dopamine Receptors Synergy in Striatum: Effects of Intrastriatal Infusions of dopamine agonists and antagonists on immediate early gene expression", Neuroscience 1995, vol. 66, No. 4, p. 903-913.

Sugahara et al. "Dopamine D1 and D2 receptor agents and their interaction influence the synaptic density of the rat prefrontal cortex", Neuroscience Letters 1999, vol. 259, p. 141-144.

Tang et al. "A synergistic interaction between dopamine D1 and D2 receptor subtypes in the memory impairments induced by concussive brain injury (CBI) in mice", Behavioural Brain Research 1997, vol. 83, p. 189-193.

Lee et al. "Dopamine D1 and D2 Receptor Co-activation Generates a Novel Phospholipase C-mediated Calcium Signal", The Journal of Biological Chemistry 2004, vol. 279, No. 34, p. 35671-35678.

Rashid et al. "D1-D2 dopamine receptor heterooligomers with unique pharmacology are coupled to rapid activation of Gq/11 in the striatum", PNAS Jan. 9, 2007, vol. 104, No. 2, p. 654-659.

Surmeier et al. "Are neostriatal dopamine receptors co-localized?", TINS 1993, vol. 16, No. 8, p. 299-305.

Vincent et al. "Cellular Colocalization of Copamine D1 and D2 Receptors in Ray Medial Prefrontal Cortex", SYNAPSE 1995, vol. 19, p. 112-120.

Lee et al. "Dual Regulation of NMDA Receptor Functions by Direct Protein-Protein Interactions with the Dopamine D1 Receptor", Cell Oct. 18, 2002, vol. 111, p. 219-230.

So et al. "Desensitization of the Dopamine D1 and D2 Receptor Hetero-Oligomer Mediated Calcium by Agonist Occupancy of Either Receptor", Molecular Pharmacology 2007, vol. 72, No. 2, p. 450-462.

Edwards et al. "Neurochemical and Behavioral Consequences of Mild, Uncontrollable Shock: Effects of PCPA", Pharmacology Biochemistry & Behavior 1986, vol. 25, p. 415-421.

Setnik et al. "Increased homocysteine levels associated with sex and stress in the learned helplessness model of depression", Pharmacology Biochemistry and Behavior 2004, vol. 77, p. 155-161.

D'Aquila et al. "Anti-anhedonic actions of the novel serotonergic agent flibanserin, a potential rapidly-acting antidepressant", European Journal of Pharmacology 1997, vol. 340, p. 121-132.

Kapur et al. "Antipsychotic Dosing in Preclinical Models is Often Unrepresentative of the Clinical Condition: A Suggested Solution Based on in Vivo Occupancy", The Journal of Pharmacology and Experimental Therapeutics 2003, vol. 305, No. 3, p. 625-631.

Detke et al. "Blockade of the antidepressant-like effects of 8-OH-DPAT, buspirone and desipramine in the rat forced swim test by 5HT1A receptor antagonists", Psychopharmacology 1995, vol. 119, p. 47-54.

Chen et al. "Roles of Dopamine Receptors in Long-Term Depression: Enhancement via D1 Receptors and Inhibition via D2 Receptors", Receptors and Channels 1996, vol. 4, p. 1-8.

Tijssen. "Overview of principles of hybridization and the strategy of nucleic acid probe assays", In Laboratory Techniques in Biochemistry and molecular biology: hybridization with nucleic acid probes, vol. 24, Amsterdam, The Netherlands, Elsevier Science Publishers BV, 1993, p. 19-78.

Baldessarini. "Drug Therapy of Depression and Anxiety Disorders", Goodman & Gilman's The Pharmacological Basis of Therapeutics, Ch.17 (2006), p. 429-459.

Steinbusch. "Serotonin-immunoreactive neurons and their projections in the CNS", Handbook of Chemical Neuroanatomy vol. 3: Classical Transmitters and Transmitter Receptors in the CNS, Part II (1984), p. 68-125.

Stephens et al. "The Economic Burden of Mental Health Problems in Canada", Chronic Diseases in Canada vol. 22, No. 1 (2001), p. 18-23.

* cited by examiner

IP: anti-D2

Anti-D2

Anti-D1

Control     haloperidol

```
MDPLNLSWYD DDLERQNWSR PFNGSDGKAD RPHYNYYATL LTLLIAVIVF  50
GNVLVCMAVS REKALQTTTN YLIVSLAVAD LLVATLVMPW VVYLEVVGEW 100
KFSRIHCDIF VTLDVMMCTA SILNLCAISI DRYTAVAMPM LYNTRYSSKR 150
RVTVMISIVW VLSFTISCPL LFGLNNADQN ECIIANPAFV VYSSIVSFYV 200
PFIVTLLVYI KIYIVLRRRR KRVNTKRSSR AFRAHLRAPL KGNCTHPEDM 250
KLCTVIMKSN GSFPVNRRRV EAARRAQELE MEMLSSTSPP ERTRYSPIPP 300
SHHQLTLPDP SHHGLHSTPD SPAKPEKNGH AKDHPKIAKI FEIQTMPNGK 350
TRTSLKTMSR RKLSQQKEKK ATQMLAIVLG VFIICWLPFF ITHILNIHCD 400
CNIPPVLYSA FTWLGYVNSA VNPIIYTTFN IEFRKAFLKI LHC        443
```

(SEQ ID NO:5)

Figure 11

```
atggatccac tgaatctgtc ctggtatgat gatgatctgg agaggcagaa ctggagccgg   60
cccttcaacg ggtcagacgg gaaggcggac agacccact acaactacta tgccacactg  120
ctcaccctgc tcatcgctgt catcgtcttc ggcaacgtgc tggtgtgcat ggctgtgtcc  180
cgcgagaagg cgctgcagac caccaccaac tacctgatcg tcagcctcgc agtggccgac  240
ctcctcgtcg ccacactggt catgcctgg gttgtctacc tggaggtggt aggtgagtgg  300
aaattcagca ggattcactg tgacatcttc gtcactctgg acgtcatgat gtgcacggcg  360
agcatcctga acttgtgtgc catcagcatc gacaggtaca cagctgtggc catgcccatg  420
ctgtacaata cgcgctacag ctccaagcgc cgggtcaccg tcatgatctc catcgtctgg  480
gtcctgtcct tcaccatctc ctgcccactc ctcttcggac tcaataacgc agaccagaac  540
gagtgcatca ttgccaaccc ggccttcgtg gtctactcct ccatcgtctc cttctacgtg  600
cccttcattg tcaccctgct ggtctacatc aagatctaca ttgtcctccg cagacgccgc  660
aagcgagtca acaccaaacg cagcagccga gctttcaggg cccacctgag ggctccacta  720
aagggcaact gtactcaccc cgaggacatg aaactctgca ccgttatcat gaagtctaat  780
gggagtttcc cagtgaacag gcggagagtg gaggctgccc ggcgagccca ggagctggag  840
atggagatgc tctccagcac cagcccaccc gagaggaccc ggtacagccc catcccaccc  900
agccaccacc agctgactct ccccgacccg tcccaccatg gtctccacag cactcccgac  960
agccccgcca aaccagagaa gaatgggcat gccaaagacc accccaagat tgccaagatc 1020
tttgagatcc agaccatgcc caatggcaaa acccggacct ccctcaagac catgagccgt 1080
aggaagctct cccagcagaa ggagaagaaa gccactcaga tgctcgccat tgttctcggc 1140
gtgttcatca tctgctggct gcccttcttc atcacacaca tcctgaacat acactgtgac 1200
tgcaacatcc cgcctgtcct gtacagcgcc ttcacgtggc tgggctatgt caacagcgcc 1260
gtgaacccca tcatctacac caccttcaac attgagttcc gcaaggcctt cctgaagatc 1320
ctccactgct ga                                                     1332
```

(SEQ ID NO:6)

Figure 12

```
MRTLNTSAMD GTGLVVERDF SVRILTACFL SLLILSTLLG NTLVCAAVIR  50
FRHLRSKVTN FFVISLAVSD LLVAVLVMPW KAVAEIAGFW PFGSFCNIWV 100
AFDIMCSTAS ILNLCVISVD RYWAISSPFR YERKMTPKAA FILISVAWTL 150
SVLISFIPVQ LSWHKAKPTS PSDGNATSLA ETIDNCDSSL SRTYAISSSV 200
ISFYIPVAIM IVTYTRIYRI AQKQIRRIAA LERAAVHAKN CQTTTGNGKP 250
VECSQPESSF KMSFKRETKV LKTLSVIMGV FVCCWLPFFI LNCILPFCGS 300
GETQPFCIDS NTFDVFVWFG WANSSLNPII YAFNADFRKA FSTLLGCYRL 350
CPATNNAIET VSINNNGAAM FSSHHEPRGS ISKECNLVYL IPHAVGSSED 400
LKKEEAAGIA RPLEKLSPAL SVILDYDTDV SLEKIQPITQ NGQHPT     446
```

(SEQ ID NO:7)

Figure 13

```
atgaggactc tgaacacctc tgccatggac gggactgggc tggtggtgga gagggacttc  60
tctgttcgta tcctcactgc ctgtttcctg tcgctgctca tcctgtccac gctcctgggg 120
aacacgctgg tctgtgctgc cgttatcagg ttccgacacc tgcggtccaa ggtgaccaac 180
ttctttgtca tctccttggc tgtgtcagat ctcttggtgg ccgtcctggt catgccctgg 240
aaggcagtgg ctgagattgc tggcttctgg ccctttgggt ccttctgtaa catctgggtg 300
gcctttgaca tcatgtgctc cactgcatcc atcctcaacc tctgtgtgat cagcgtggac 360
aggtattggg ctatctccag ccctttccgg tatgagagaa agatgacccc caaggcagcc 420
ttcatcctga tcagtgtggc atggaccttg tctgtactca tctccttcat cccagtgcag 480
ctcagctggc acaaggcaaa acccacaagc ccctctgatg gaaatgccac ttccctggct 540
gagaccatag acaactgtga ctccagcctc agcaggacat atgccatctc atcctctgta 600
ataagctttt acatccctgt ggccatcatg attgtcacct acaccaggat ctacaggatt 660
gctcagaaac aaatacggcg cattgcggcc ttggagaggg cagcagtcca cgccaagaat 720
tgccagacca ccacaggtaa tggaaagcct gtcgaatgtt ctcaaccgga aagttctttt 780
aagatgtcct tcaaaagaga aactaaagtc ctgaagactc tgtcggtgat catgggtgtg 840
tttgtgtgct gttggctacc tttcttcatc ttgaactgca ttttgccctt ctgtgggtct 900
ggggagacgc agcccttctg cattgattcc aacacctttg acgtgtttgt gtggtttggg 960
tgggctaatt catccttgaa ccccatcatt tatgccttta atgctgattt tcggaaggca 1020
ttttcaaccc tcttaggatg ctacagactt tgccctgcga cgaataatgc catagagacg 1080
gtgagtatca ataacaatgg ggccgcgatg ttttccagcc atcatgagcc acgaggctcc 1140
atctccaagg agtgcaatct ggtttacctg atcccacatg ctgtgggctc ctctgaggac 1200
ctgaaaaagg aggaggcagc tggcatcgcc agacccttgg agaagctgtc cccagcccta 1260
tcagtcatat tggactatga cactgacgtc tctctggaga agatccaacc catcacacaa 1320
aacggtcagc acccaacctg a                                           1341
```

(SEQ ID NO:8)

Figure 14

POLYPEPTIDES AND METHODS FOR MODULATING D1-D2 DOPAMINE RECEPTOR INTERACTION AND FUNCTION

CROSS-REFERENCE TO RELATED APPLICATIONS

This application is the U.S. National Phase of PCT Appl. No. PCT/CA2009/000829 filed Jun. 12, 2009, now expired, which claims priority to U.S. provisional application Serial No. 61/060,948 filed Jun. 12, 2008, the disclosures of which are incorporated in their entirety *by* reference *herein*.

SEQUENCE LISTING

The text file titled "Sequence Listing.txt" of size 14.4 KB, filed herewith, is hereby incorporated by reference.

FIELD OF INVENTION

The present invention relates to psychiatric diseases or disorders, and more particularly, compositions and methods for modulating the interaction and function of D1-D2 dopamine receptors. Such compositions and methods are useful for prevention and/or treatment of psychiatric diseases or disorders, particularly depression, including major depressive illness and depression in bipolar disorder, and psychiatric conditions that require treatment with medication, including schizophrenia, psychosis in bipolar disorder, and stimulant drug intoxication.

BACKGROUND OF THE INVENTION

Depression:

Depression is a mood disorder characterized by depressed mood; feelings of worthlessness, helplessness or hopelessness; a loss of interest or pleasure; changes in appetite; change in sleeping pattern; fatigue, thoughts of death, inability to concentrate or make decisions. According to Statistics Canada's 2002 Mental Health and Well-being Survey[4], 12.2% of all Canadians will experience depression within their lifetime, while 4.8% of Canadians had reported symptoms for major depression. Furthermore, the economical impact of depression is tremendous due to costs in both productivity and health care. In Canada, between 62% and 76% of short-term disability episodes due to mental disorders were attributed to depression[5]. Work-related productivity losses due to depression have been estimated to be $4.5 billion[6]. Thus, the prevalence of depression makes this disorder a very important health issue in Canada and abroad.

Once diagnosed, depression can be treated by different therapies including medication, psychotherapy and in more severe cases, with electroconvulsive therapy. The first line of treatment is often through antidepressant medication, sometimes in conjunction with psychotherapy. Antidepressants consist of the classical tricyclic antidepressants (TCA), selective serotonin reuptake inhibitors (SSRI), noradrenaline and serotonin reuptake inhibitor (NSRI), as well as monoamine oxidase inhibitors (MAOI). All antidepressants have acute effects on synaptic levels of neurotransmitters in the brain[7-9]. The classical TCAs are predominantly noradrenaline and serotonin reuptake inhibitors, similar to NSRIs. The SSRI drugs are more selective serotonin transporter inhibitors, while MAOI block enzymes that are involved in the breakdown of these neurotransmitters.

Dopamine (DA), acting through DA receptors, exerts a major role in regulating neuronal motor control, cognition, event prediction, emotion and pleasure/reward[10-15], all of which are affected in depression. The contribution of DA in depression becomes evident when taking into account the major dopaminergic pathways in the mammalian brain: (a) the mesostriatal system consisting of dopaminergic neurons from the substantia nigra (SNc) innervating the striatum; (b) the mesolimbic system in which dopaminergic neurons from the ventral tegmental area (VTA) project into the hippocampus, nucleus accumbens (NAc) and amygdala; (c) the mesocortical system where DA neurons mostly from the VTA project into the cortical regions of the brain including the prefrontal cortex (PFx). Most of these regions have been implicated in depression. Furthermore, numerous studies support the hypothesis of decreased dopaminergic signalling in depression including reports that: (1) the severity of major depression correlates highly with patient response to amphetamine, a drug that facilitates increased synaptic DA levels through multiple mechanisms[16], while another study has shown decreased levels of homovanillic acid, a major DA metabolite, in the CSF of depression patients[17]; (2) animals experiencing learned helplessness, a behavioural paradigm that recapitulates some of the symptoms of depression, have been shown to exhibit DA depletion in the striatum, which can be mitigated by pretreatments with DA agonists[18-19]; (3) motor effects induced by DA receptor agonists are increased after chronic treatment with antidepressants or electroconvulsive therapy[20] suggesting reduced dopaminergic neurotransmission in depression; (4) in forced-swim tests, DA agonists have been shown to inhibit immobility, an indication of antidepressant activity, while DA receptor antagonists have been shown to inhibit the effects of antidepressants[21-32]; (5) DAT inhibitors nomifensine and bupropion have been shown to be effective antidepressants[21, 33-34] and (6) clinical studies have also documented cases where DA receptor agonists have been effective in treating depression[35-39]. Furthermore, there is some evidence from neuroimaging studies that dopamine D2 receptor (D2R) are elevated in the striatum of depressed patients[40-44].

Another brain pathway implicated in depression is the hypothalamic-pituatary-adrenal (HPA) axis. The HPA axis is involved in stress reaction and ultimately leads to increased secretion of glucocorticoids from the adrenal cortex. Although glucocorticoids have effects on the hippocampus it has also been shown to facilitate DA transmission in NAc[45]. In addition, frequent bouts of stress with intermittent exposure to glucocorticoids sensitize the mesolimbic DA system[46]. While the hippocampus and frontal cortex are undoubtedly involved in certain aspects of depression, symptoms of anhedonia, lack of motivation and motor deficits implicate other regions of the brain including the dorsal and ventral striatum, which are rich in dopaminergic neurons. Moreover, serotonergic activity has an impact on DA neurotransmission. Studies have shown that stimulation of $5HT_{1A}$ receptors can stimulate DA release in PFx and NAc but inhibit DA release in the dorsal striatum[47]. Other studies have shown that activation of serotonergic raphe neurons reduces activity of dopaminergic neurons in VTA (not SNc) and inhibit locomotion, exploratory behaviour[48-49].

Schizophrenia:

Schizophrenia is a severe chronic and debilitating mental disorder that strikes in youth and affects not only patients but their families and care-givers[50-51]. Approximately 2.2 million American adults have schizophrenia in a given year. Clinical symptoms of schizophrenia include delusions, hallucinations, disorganized thinking, and cognitive dysfunction that are divided into two major groups: positive and negative symptoms[52].

Accumulated evidence suggests that the positive symptoms result from hyperdopaminergia involving dopamine D2 receptors in the limbic striatum, while the negative/cognitive symptoms arise from a hypodopaminergic function mediated by dopamine D1 receptors in the prefrontal cortex[52]. Despite decades of intensive research, current antipsychotic medications are still limited to the blockade of D2 receptor function that generally alleviate positive symptoms with only limited impact on cognitive and negative symptoms and can induce serious side effects including extrapyramidal side effects (EPS). Patients continue to experience significant disability and functional impairment that limits their integration in society. The unavailability of effective medications with both D1 agonism and D2 antagonism is mainly due to the unknown therapeutic target, a pathway through which both inhibition of D2 receptor and activation of D1 receptor function can be achieved.

The dopamine hypothesis of schizophrenia, in its original formulation addressed mainly positive symptoms[53-54]. Early pharmacotherapy for schizophrenia involved the use of reserpine, which blocks dopamine release from presynaptic terminals, and/or the use of antipsychotics[55]. Moreover, the most compelling evidence for the involvement of dopamine receptors in schizophrenia comes from the fact that most antipsychotics, including atypical antipsychotics, show a dose-dependent threshold of D2 receptor occupancy for their therapeutic effects[55]. The efficacy of both reserpine and antipsychotics in treating schizophrenia strongly implicate the involvement of dopamine in this neuropsychiatric disorder. More recent versions of this theory suggests that while the positive symptoms result from hyperdopaminergia in the limbic striatum, the negative/cognitive symptoms arise from a hypodopaminergic function in the prefrontal cortex (PFC)[56-57]. A significant body of literature lends support to this theory. PET & SPECT studies have shown evidence of increased dopamine synthesis, release, and levels in the subcortical/limbic regions[58] while functional imaging studies have demonstrated hypofunction in the prefrontal cortex at baseline and while performing cognitive tasks[59]. More recent studies have focused on the dopamine D1 system in the PFC, as it is the predominant dopamine receptor sub-type in the PFC[60-61], and show a decrease in receptor number which correlates with executive dysfunction[62] and a compensatory up-regulation which correlates with working-memory dysfunction[63]. These clinical observations are well supported by preclinical evidence—PFC D1 receptor modulation changes the 'memory fields' of prefrontal neurons subserving working memory[64-65] and D1 agonist administration improves working memory performance in both aging and dopamine deficient monkeys[66] (as it does in aging human subjects)[67-68].

Overview of DA Receptors:

In mammals, five distinct genes, termed D1/D5 for D1-like receptors and D2/D3/D4 for D2-like receptors, encode DA receptors. These receptors belong to a super-family of single polypeptide seven trans-membrane (TM) domain receptors that exert their biological effects via intracellular G-protein coupled signaling cascades[1]. D1 and D5 receptors preferentially couple to Gs proteins stimulating the activity of adenylate cyclase and PKA dependent pathways. D2 receptors display a more complex pattern of signal transduction primarily due to their coupling to subtype specific members of the Gi/Go protein family.

D2 receptors are known to stimulate a number of signal transduction pathways including the inhibition of adenylate cyclase activity, PI turnover, potentiation of arachidonic acid release, inwardly rectifying $K^+$ and $Ca^{2+}$ channels and mitogen activated protein kinases[2]. Moreover, studies have shown that protein interactions can play a large role in DA receptor function. For instance, the D2R has been shown to physically interact with Par-4. Interestingly, Par-4 mutant mice, which are unable to interact with D2R, exhibit depression-like behaviour[3].

Dopamine D1-D2 Receptor Link:

While numerous studies have indicated a synergy between D1 and D2 receptors, an interesting study by Seeman et al (1989)[69] provided the first evidence of a pharmacological link between D1 and D2 receptors. Briefly, it was shown that dopamine could lower the density of D2 receptors labeled by [$^3$H] raclopride and that the addition of the specific D1 receptor antagonist, SCH-23390, prevented this reduction, suggesting a functional link between D1 and D2 receptors. Interestingly, this pharmacological D1-D2 link was absent or reduced in post-mortem brain tissues of approximately half of the schizophrenia population tested. However, it remains unclear if the absence of the D1-D2 link is due to an inherent dissociation between the D1 and D2 receptor that occurs in schizophrenia or is a result of anti-psychotic drug treatment. Furthermore, several studies using a combination of D1 and D2 specific agonists and/or antagonists have shown that co-activation of D1-D2 receptors are required for long-term depression, anandamide-mediated memory consolidation and potentiation of immediate early gene response, suggesting a potential functional interaction between the D1R and D2R[70-76].

Recent evidence indicates that D1 and D2 receptors form a protein complex, and co-activation of D1 and D2 receptors results in an increase of intracellular calcium levels via a signaling pathway not activated by either receptor alone, confirming the functional link observed between D1 and D2 receptors[77-78]. Furthermore, it has been shown that D1 and D2 receptors are co-expressed in neurons of the rat striatum, providing a basis for a functional interaction[79-80].

Despite years of research in the field of mental health, there continues to be a need for new and improved medicines for treating psychiatric diseases and disorders, including depression, schizophrenia and psychotic symptoms thereof. The present inventors have accordingly sought to identify new diagnostic and chemotherapeutic methods in this area by investigating the functional association between D1 and D2 classes of DA receptors.

SUMMARY OF THE INVENTION

The present invention accordingly relates to compositions and methods for prevention and/or treatment of diseases and disorders involving abnormal DA receptor association and functionality. More particularly, the present invention relates to methods of modulating the interaction and functionality of D1-D2 receptors, as well as compounds useful in such methods. The invention also relates to methods of diagnosis of diseases and disorders caused by abnormal D1-D2 receptor association and functionality.

The present invention provides compounds, compositions and methods for modulating the interaction of D1-D2 receptors. Furthermore, the present invention provides methods for preventing and/or treating diseases involving abnormal levels of D1-D2 interaction and/or functionality.

According to the present invention there is provided a method for modulating dopamine (DA) receptor function in a mammal in need of such treatment comprising administering a therapeutically effective amount of an agent that disrupts D1-D2 coupling in the mammal. In a preferred embodiment, which is not meant to be limiting in any manner, the agent is a peptide or polypeptide.

In an embodiment, the agent is an antibody that binds to an amino acid sequence that is at least 80% identical to the sequence of any one of the sequences selected from $D2_{IL3\text{-}29}$ (SEQ ID NO:1), $D2L_{IL3\text{-}29\text{-}2}$ (SEQ ID NO:2), $D2_{IL3\text{-}L}$ (SEQ ID NO:3), and $D1_{CT}$ (SEQ ID NO:4). In a further embodiment, the amino acid sequence is identical to the sequence of $D2_{IL3\text{-}29}$ (SEQ ID NO:1), $D2L_{IL3\text{-}29\text{-}2}$ (SEQ ID NO:2), $D2_{IL3\text{-}L}$ (SEQ ID NO:3), or $D1_{CT}$ (SEQ ID NO:4).

In a further embodiment, the agent is a nucleic acid encoding a polypeptide of between about 3 and about 140 amino acids and comprising an amino acid sequence that is at least 80% identical to the sequence of any one of the sequences selected from $D2_{IL3\text{-}29}$ (SEQ ID NO:1), $D2L_{IL3\text{-}29\text{-}2}$ (SEQ ID NO:2), $D2_{IL3\text{-}L}$ (SEQ ID NO:3), and $D1_{CT}$ (SEQ ID NO:4). The polypeptide, in some embodiments, may be identical to a sequence of $D2_{IL3\text{-}29}$ (SEQ ID NO: 1), $D2L_{IL3\text{-}29\text{-}2}$ (SEQ ID NO:2), $D2_{IL3\text{-}L}$ (SEQ ID NO:3), and $D1_{CT}$ (SEQ ID NO:4).

In further embodiments, the agent may be a polypeptide of between about 3 and about 140 amino acids comprising an amino acid sequence that is between about 80% and about 100% identical to any one of the sequences selected from the group consisting of $D2_{IL3\text{-}29}$ (SEQ ID NO:1), $D2L_{IL3\text{-}29\text{-}2}$ (SEQ ID NO:2), $D2_{IL3\text{-}L}$ (SEQ ID NO:3), and $D1_{CT}$ (SEQ ID NO:4). The polypeptide, in such embodiments, may be identical to a sequence of $D2_{IL3\text{-}29}$ (SEQ ID NO:1), $D2L_{IL3\text{-}29\text{-}2}$ (SEQ ID NO:2), $D2_{IL3\text{-}L}$ (SEQ ID NO:3), and $D1_{CT}$ (SEQ ID NO:4).

The above method can be for preventing and/or treating a disease selected from the group consisting of depression, including major depressive illness and depression in bipolar disorder, and psychiatric conditions that require treatment with antipsychotic medication, including schizophrenia, psychosis in bipolar disorder, and stimulant drug intoxication.

As a further aspect of the invention, there is provided a polypeptide of between about 3 and about 140 amino acids comprising an amino acid sequence that is at between about 80% and about 100% identical to the sequence of $D2_{IL3\text{-}29}$ (SEQ ID NO: 1), $D2L_{IL3\text{-}29\text{-}2}$ (SEQ ID NO:2), $D2_{IL3\text{-}L}$ (SEQ ID NO:3), and $D1_{CT}$ (SEQ ID NO:4).

The polypeptide may comprise an amino acid sequence that is between about 80% and 100% identical to a sequence selected from the group consisting of $D2_{IL3\text{-}29}$ (SEQ ID NO: 1), $D2L_{IL3\text{-}29\text{-}2}$ (SEQ ID NO:2), $D2_{IL3\text{-}L}$ (SEQ ID NO:3), and $D1_{CT}$ (SEQ ID NO:4). More specifically, the polypeptide may comprise an amino acid sequence that is identical to $D2_{IL3\text{-}29}$ (SEQ ID NO:1), $D2L_{IL3\text{-}29\text{-}2}$ (SEQ ID NO:2), $D2_{IL3\text{-}L}$ (SEQ ID NO:3), or $D1_{CT}$ (SEQ ID NO:4).

In a yet further aspect of the invention, there is provides a nucleic acid encoding a polypeptide of between 3 and 140 amino acids comprising an amino acid sequence that is between about 80% identical and 100% identical to the sequence of $D2_{IL3\text{-}29}$ (SEQ ID NO:1), $D2L_{IL3\text{-}29\text{-}2}$ (SEQ ID NO:2), $D2_{IL3\text{-}L}$ (SEQ ID NO:3), and $D1_{CT}$ (SEQ ID NO:4).

The nucleic acid may encode a polypeptide having an amino acid sequence that is between 80% and 100% identical to a sequence selected from the group consisting of $D2_{IL3\text{-}29}$ (SEQ ID NO:1), $D2L_{IL3\text{-}29\text{-}2}$ (SEQ ID NO:2), $D2_{IL3\text{-}L}$ (SEQ ID NO:3), and $D1_{CT}$ (SEQ ID NO:4). In a further embodiment, the nucleic acid encodes a polypeptide that is identical to a sequence selected from $D2_{IL3\text{-}29}$ (SEQ ID NO:1), $D2L_{IL3\text{-}29\text{-}2}$ (SEQ ID NO:2), $D2_{IL3\text{-}L}$ (SEQ ID NO:3), and $D1_{CT}$ (SEQ ID NO:4).

A protein transduction domain may be fused or linked to any small molecule chemical compound, polypeptide, nucleic acid, or combination thereof, used in the context of the present invention. In certain non-limiting representative examples, the protein transduction domain is selected from the group consisting of TAT, and SynB1/3Cit. Also, other proteins, non-protein carriers or other macromolecules may be attached or conjugated to the compound, polypeptide, nucleic acid described above.

The present invention also provides a kit comprising any component or combination of components as mentioned or described throughout.

As described herein, a direct interaction between D1 and D2 receptors, has been identified, and the present invention provides agents that specifically disrupt this interaction. Furthermore, the present invention provides methods for identifying agents that disrupt the interaction between the D1 and D2 receptors.

This summary of the invention does not necessarily describe all features of the invention.

BRIEF DESCRIPTION OF THE DRAWINGS

These and other features of the invention will become more apparent from the following description in which reference is made to the appended drawings, in which:

FIG. 1A shows the results of a Western blot analysis in which CO-IP of D1 receptor by D2 receptor (antibody) in solubilized rat striatal tissue;

FIG. 1B shows the results of a Western blot analysis in which D2 receptor is specifically pulled down by GST-$D1_{CT}$ in detergent extracts of rat striatum, but not GST-$D1_{IL3}$ (third intracellular loop) or GST alone;

FIG. 1C shows the results of a Western blot analysis in which D1 receptor was specifically pulled down by GST-$D2_{IL3\text{-}L}$ in detergent extracts of rat striatum, but not GST-$D2_{IL3\text{-}S}$ or GST alone;

FIG. 1D shows the results of a Western blot analysis in which D1 receptor was specifically pulled down by GST-$D2_{IL3\text{-}L}$ and GST-$D2_{IL3\text{-}29}$ in detergent extracts of rat striatum, but not GST-$D2_{CT}$, GST-$D2_{IL3\text{-}S}$ or GST alone;

FIG. 1E shows the results of a Western blot analysis in which D1 receptor was pulled down by GST-$D2_{IL3\text{-}29\text{-}2}$, but not GST-$D2_{IL3\text{-}29\text{-}1}$ or GST alone;

FIG. 1F shows the results of a Western blot analysis of an in vitro binding assay, wherein a $S^{35}$-D1 tail probe specifically bound with GST-$D2_{IL3\text{-}29\text{-}2}$ fragment, but not with GST-$D2_{IL3\text{-}29\text{-}1}$ or GST alone;

FIG. 1G shows the results of a Western blot analysis of competitive CO-IP in rat striatum. The ability of D1 receptor to co-immunoprecipitate with D2 receptor is inhibited by the addition of GST-$D2_{IL3\text{-}29\text{-}2}$ in a concentration dependent manner;

FIG. 2A shows the results of a time course of 2 μM Fluo-4AM fluorescence, corresponding to increases in intracellular $Ca^{2+}$ levels in HEK-293T cells co-expressing D1 and D2 receptors, following simultaneous activation by both 10 μM SKF81297 and quinpirole. Fluorescence values were monitored using a PerkinElmer multiwell plated fluorometer, collected at 3-s intervals for 150 s. (A.F.U.: arbitrary fluorescence units). The curve shown is representative of three replicate measurements performed;

FIG. 2B shows the measurement of fluorescence, corresponding to the intracellular $Ca^{2+}$ levels in HEK-293T cells co-expressing D1 and D2 receptors treated with 10 μM SKF81297, 10 μM quinpirole or both. ** Significant vs. control group ($p<0.01$). Significant vs. SKF+Quin group (#, $p<0.05$; ##, $p<0.01$). Data is representative of three replicate measurements performed. Data was analyzed by one-way ANOVA, followed by Newman-Keuls test;

FIG. 3A shows fluorescence measurements for HEK-293T cells co-expressing D1 and D2 receptors and pretreated with 10 μM raclopride or SCH23390. The cells were stimulated with both 10 μM SKF81297 and 10 μM quinpirole. Significant vs. control group (*, p<0.05; **, p<0.01). ### Significant vs. SKF+Quin group (p<0.001) Data is representative of three replicate measurements performed. Data was analyzed by one-way ANOVA, followed by Newman-Keuls test;

FIG. 3B shows fluorescence measurements for HEK-293T cells co-expressing D1 and D2 receptors and pretreated with 10 μM U73122 (PLC inhibitor). The cells were stimulated with 10 μM SKF81297 and 10 μM quinpirole. Significant vs. control group (**, p<0.01). ### Significant vs. SKF+Quin group (p<0.001). Data is representative of three replicate measurements performed. Data was analyzed by one-way ANOVA, followed by Newman-Keuls test;

FIG. 3C shows fluorescence measurements for HEK-293T cells co-expressing D1 and D2 receptors in the presence of $D1_{CT}$ or $D5_{CT}$ mini-genes and stimulated with a 10 μM concentration of both SKF81297 and quinpirole. *, ** Significantly from control group (p<0.05; p<0.01). #Significantly from SKF+Quin group (p<0.05). Data is representative of three replicate measurements performed. Data was analyzed by one-way ANOVA, followed by Newman-Keuls test;

FIG. 4 shows the results of characterization of the D1-D2 interaction in post-mortem brain. Striatal post-mortem brain samples (control, schizophrenia, bipolar and depression; 15 samples in each group), obtained from the Stanley Foundation, were incubated with anti-D2 receptor antibodies for coimmunoprecipitation experiments. Precipitated proteins were subject to SDS-PAGE; immunoblotted with D1 antibody. Co-immunoprecipitation of D1 by the D2 antibody is significantly increased in depression brains compared to controls. Data were analyzed by one-way ANOVA followed by post-hoc SNK tests (* P<0.05, n=15);

FIG. 5 illustrates the results of an analysis of D1-D2 interaction, in which it is shown that chronic antidepressant treatment results in a decrease in D1-D2 interaction. Rats were treated with imipramine (IMI, 10 mg/kg/day) or saline for 14 days. On the 14th day, rats were sacrificed, brains quickly extracted and striata were dissected for biochemical analysis. (A) Striata were solubilized and used in coimmunoprecipitation experiments to examine the coprecipitation of the D1 receptor with the D2 receptor. Rats subjected to chronic imipramine (IMI) exhibited a decrease in the D1-D2 interaction, as quantified from Western blots of co-immunoprecipitation samples (*, p<0.05, t-test, n=5). Quantification of Western blots from the control (Con) and IMI samples revealed no significant differences in either D1 receptor levels (B), or D2 receptor levels (C) (n=5). Tubulin was used as loading controls;

FIG. 6 illustrates the results of a study of rats subjected to learned helplessness (LH), in which an increase in the D1-D2 interaction is shown. Rats that were subjected to LH were compared against control rats. (A) Striata were solubilized and used in co-immunoprecipitation experiments to examine the co-precipitation of the D1 receptor with the D2 receptor. Rats exhibited an increase in the D1-D2 interaction after LH, as quantified from Western blots of co-immunoprecipitation samples (**, p<0.01, n=5, t-test). (B) Prefrontal cortex (PFC) were solubilized and used in co-immunoprecipitation experiments to examine the co-precipitation of the D1 receptor with the D2 receptor. Rats exhibited an increase in the D1-D2 interaction after LH, as quantified from Western blots of co-immunoprecipitation samples (*, p<0.05, n=5, t-test);

FIG. 7 illustrates the results of a study of rats subjected to chronic mild stress (CMS), in which an increase in the D1-D2 interaction is shown. Rats that were subjected to CMS were compared against control rats. Prefrontal cortex were solubilized and used in co-immunoprecipitation experiments to examine the co-precipitation of the D1 receptor with the D2 receptor. Rats exhibited an increase in the D1-D2 interaction after CMS, as quantified from Western blots of co-immunoprecipitation samples (*, p<0.05, n=5, t-test).

FIG. 8 illustrates the results of a study of rats subjected to forced swim tests (FST), in which an increase in the D1-D2 interaction is shown. Rats that were subjected to forced swim tests were compared against control rats for changes in D1 and D2 receptors. (A) Rat striata were solubilized and used in co-immunoprecipitation experiments to examine the co-precipitation of the D1 receptor with the D2 receptor. Rats exhibited an increase in the D1-D2 interaction 3 hours or 3 days after FST trials, as quantified from Western blots of co-immunoprecipitation samples (*, p<0.05, n=4, ANOVA post hoc SNK). Quantification of Western blots from the control (Con) and FST samples revealed no significant differences in either D1 receptor levels (B), or D2 receptor levels (C) (n=4). Tubulin was used as loading controls;

FIG. 9 shows Western blots illustrating a significant decrease in D1-D2 receptor complex formation in rat with chronic antipsychotic treatment (bottom panel) (by pump 0.25 mg/kg/day for 2 weeks), while direct immunoprecipitated D2 receptors remain unchanged (top panel);

FIG. 10 illustrates the results of a study in which disruption of D1-D2 interaction leads to behavior changes in rats subjected to forced swim tests. Intra-PFC administration of TAT-D2L$_{IL3-29-2}$, but not TAT alone, decreased the frequencies of rat immobility and increased the frequencies of rat swimming and climbing behaviors in a 5 min forced swimming test. Each value is the mean±S.E.M. for a group of 6 rats. Data were analyzed by one-way analysis of variance (ANOVA).

FIG. 11 shows the protein sequence (SEQ ID NO:5) of human D2R-L. The $I_{256}$-$V_{270}$ region shown to be important for D1-D2 binding is underlined.

FIG. 12 shows the DNA sequence (SEQ ID NO:6) encoding the human D2R-L.

FIG. 13 shows the protein sequence (SEQ ID NO:7) of human D1R. The $D1_{CT}(A_{332}$-$T_{446})$ is shown in bold, while the third intracellular loop $D1_{IL3}$ ($R_{219}$-$K_{272}$) is underlined in the D1 sequence.

FIG. 14 shows the DNA sequence (SEQ ID NO:8) encoding human D1R.

DETAILED DESCRIPTION

Figure 1:
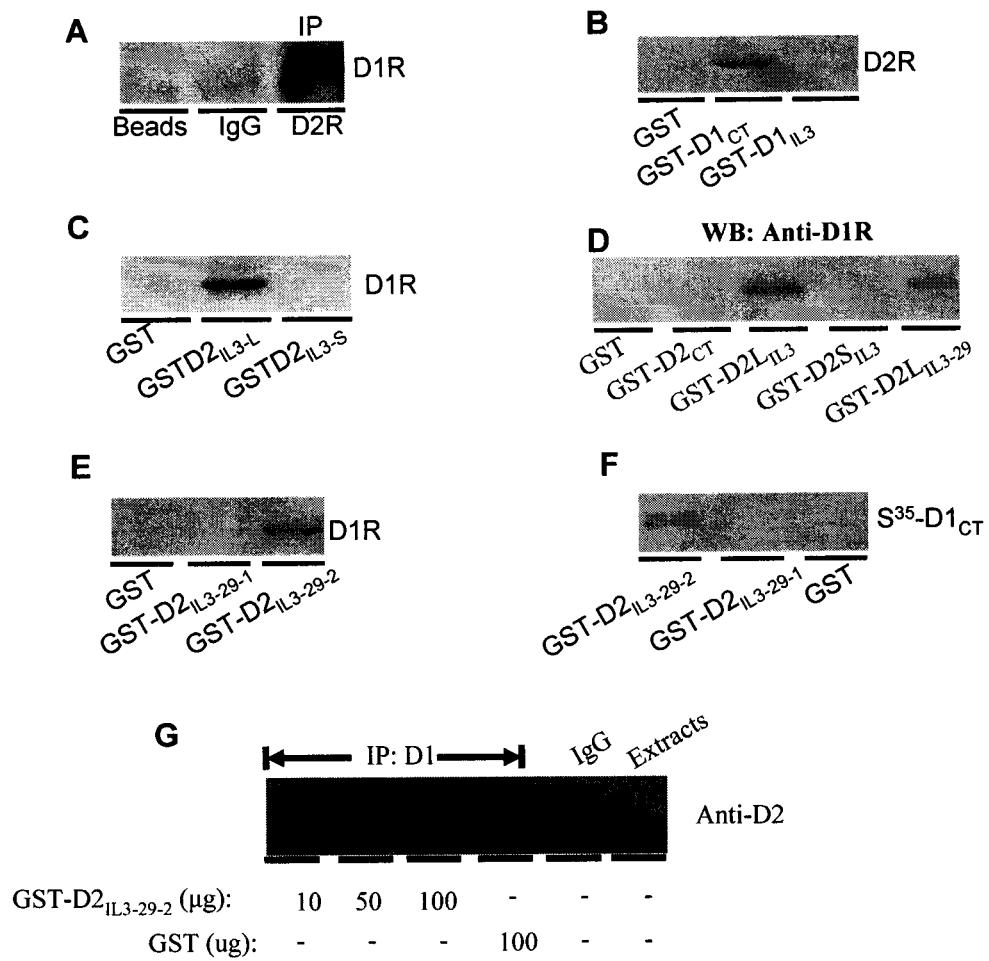

The following description is of a preferred embodiment.

The present invention provides a method for modulating dopamine (DA) receptor function, partially as a result of identifying a direct interaction between D1 and D2 receptors (see Examples). Agents that specifically disrupt the D1-D2 receptor interaction, and methods for identifying agents that disrupt this interaction are accordingly provided. Formation of the D1-D2 complex has been shown herein to occur at elevated levels in individuals suffering from depression. Moreover, disruption of the D1-D2 interaction and complex formation is shown to reduce or alleviate symptoms of depression using animal models of depression. Accordingly, modulating DA receptor function through disruption of the D1-D2 complex can be effective for preventing and/or treating a variety of neurological diseases and disorders, for example, but not limited to, depression, including major depressive illness and depression in bipolar disorder, schizophrenia, psychotic symptoms of schizophrenia, and other psychiatric conditions that require treatment with antipsychotic medication, such as psychosis in bipolar disorder, and stimulant drug intoxication.

By disrupting D1-D2 coupling, an agent may for instance inhibit binding or otherwise prevent association or interaction between the D1 and D2 receptor.

The method for modulating DA receptor function may involve administering the D1-D2 disrupting agent in a therapeutically effective amount. Such amount may vary depending upon the disease or disorder to be treated, as well as other pharmacological factors known to those skilled in the art.

It is to be understood that the polypeptide as described above does not consist of the full amino acid sequence of any naturally occurring D1 or D2 receptor, or any naturally occurring allelic variant thereof.

The sequences of $D2L_{IL3-29-2}$ (SEQ ID NO:2), $D2_{IL3-}$ (SEQ ID NO:3), and $D1_{CT}$ (SEQ ID NO:4) are as follows, with specific reference to the numbering of the full length amino acid sequences of D1 and D2 shown in FIGS. 11 and 13:

```
D2 Peptides:
D2IL3-29 G242-V270
                                                    (SEQ ID NO: 1)
GNCTHPEDMKLCTVIMKSNGSFPVNRRRV D2LIL3-29-2 I256-V270
                                                    (SEQ ID NO: 2)
IMKSNGSFPVNRRRV D2IL3-L K211-Q373
                                                    (SEQ ID NO: 3)
KIYIVLRRRRKRVNTKRSSRAFRAHLRAPLKGNCTHPEDMKLCTVIMKSNGSFPVNRRRVEAA

RRAQELEMEMLSSTSPPERTRYSPIPPSHHQLTLPDPSHHGLHSTPDSPAKPEKNGHAKDHPKIA

KIFEIQTMPNGKTRTSLKTMSRRKLSQQKEKKATQ

D1 Peptides:
D1CT A332-T446
                                                    (SEQ ID NO: 4)
AFNADFRKAFSTLLGCYRLCPATNNAIETVSINNNGAAMFSSHHEPRGSISKECNLVY

LIPHAVGSSEDLKKEEAAGIARPLEKLSPALSVILDYDTDVSLEKIQPITQNGQHPT
```

By "agent" or "agents" it is meant any small molecule chemical compound, polypeptide, nucleic acid or any combination thereof that can modulate DA receptor function. By "modulate DA receptor function" is meant an altering of function, for instance by inhibition of DA activation and/or signaling function, by disrupting D1-D2 coupling. A polypeptide may be of any length unless otherwise specified and includes, for example and without limitation, antibodies, enzymes, receptors, transporters, D2 receptor, D1 receptor fragment or derivative. A fragment is any polypeptide or nucleic acid that is shorter than its corresponding naturally occurring polypeptide or nucleic acid, respectively. A derivative is any polypeptide or nucleic acid that is altered with respect to a reference polypeptide or nucleic acid, respectively, and includes, for example fragments or mutants.

Accordingly, in a preferred embodiment, the present invention provides a polypeptide of less than 140 amino acids comprising an amino acid sequence that is at least 80% identical to the sequence of $D2_{IL3-29}$ (SEQ ID NO:1), $D2L_{IL3-29-2}$ (SEQ ID NO:2), $D2_{IL3-L}$ (SEQ ID NO:3), and $D1_{CT}$ (SEQ ID NO:4), or a fragment of any one thereof. In a preferred embodiment, the polypeptide is between about 4 and about 140 amino acids, for example, but not limited to 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 90 or 100 amino acids. In an alternate embodiment, the polypeptide is between about 3 and 100 amino acids, for example, but not limited to 5 and 100 amino acids, 7 and 100 amino acids, 9 and 100 amino acids, 11 and 100 amino acids, 13 and 100 amino acids, or 15 and about 140 amino acids, for example. However, it is to be understood that the size of the peptide may be defined by a range of any two of the values listed above or any values therein between. Also, in an alternate embodiment, which is not meant to be limiting in any manner, the present invention contemplates polypeptides as defined above which comprises more than 140 amino acids.

The present invention also contemplates polypeptides having an amino acid sequence that comprises 80%, 81%, 82%, 83%, 84%, 85%, 86%, 87%, 88%, 89%, 90%, 91%, 92%, 93%, 94%, 95%, 96%, 97%, 98%, 99% or 100% identity to the amino sequences described above. Further, the polypeptides may be defined as comprising a range of sequence identity defined by any two of the values listed above.

In an embodiment of the present invention, which is not meant to be limiting, there is provided a polypeptide from $D2L_{IL3-29-2}$ comprising or consisting of the amino acid sequence IMK, MKS, KSN, SNG, NGS, GSF, SFP, FPV, PVN, VNR, NRR, RRR, or RRV. Further, the polypeptide may comprise or consist of 4, 5, 6, 7, 8, 9, 10, 11, 12, 13, 14 or 15 amino acids including one or more sequential amino acids attached at the N terminus, C terminus or both of any of the sequences provided above that are found in a naturally occurring D2 receptor or any allelic variant thereof.

In a further embodiment of the present invention, there is provided a polypeptide comprising or consisting of the amino acid sequence from $D1_{CT}$ comprising or consisting of AFN, FNA, NAD, ADF, DFR, FRK, RKA, KAF, AFS, FST, STL, TLL, LLG, LGC, GCY, CYR, YRL, RLC, LCP, CPA, PAT, ATN, TNN, NNA, NAI, AIE, IET, ETV, TVS, VSI, SIN, INN, NNN, NNG, NGA, GAA, AAM, AMF, MFS, FSS, SSH, SHH, HHE, HEP, EPR, PRG, RGS, GSI, SIS, ISK, SKE, KEC, ECN, CNL, NLV, LVY, VYL, YLI, LIP, IPH, PHA, HAV, AVG, VGS, GSS, SSE, SED, EDL, DLK, LKK, KKE, KEE, EEA, EAA, AAG, AGI, GIA, IAR, ARP, RPL, PLE, LEK, EKL, KLS, LSP, SPA, PAL, ALS, LSV, SVI, VIL, ILD, LDY, DYD, YDT, DTD, TDV, DVS, VSL, SLE, LEK, EKI, KIQ, IQP, QPI, PIT, ITQ, TQN, QNG, NGQ, GQH, QHP, and HPT. Further, the polypeptide may comprise or consist of 4, 5, 6, 7, 8, 9, 10, 11, 12, 13, 14 or 15 amino acids including one or more sequential amino acids attached at the N terminus, C terminus or both of any of the sequences provided above that are found in a naturally occurring D1 receptor or any allelic variant thereof The present invention also provides a nucleic acid encoding polypeptides as defined above. For example, but not wishing to be limiting in any manner, the present invention contemplates a nucleic acid encoding a polypeptide of between about 3 and less than 140 amino acids, for example, but not limited to between 10 and 135 amino acids, between 10 and 100 amino acids, between 15 and 109 amino acids or between 15 and 100 amino acids and that encodes an amino acid sequence that is at least 80% identical to the sequence of $D2L_{IL3\text{-}29\text{-}2}$ (SEQ ID NO:2), $D2_{IL3\text{-}}$ (SEQ ID NO:3), and $D1_{CT}$ (SEQ ID NO:4). In an alternate embodiment, the present invention contemplates nucleic acids or nucleotide sequences as described above but that encode more than 140 amino acids. Such nucleic acids may be derived from the amino acid sequences above, or from the corresponding full length nucleic acid sequences of the D1 and/or D2 receptor coding sequences shown in FIGS. 12 and 14.

By "percent identical" or "percent identity", it is meant one or more than one nucleic acid or amino acid sequence that is substantially identical to a coding sequence or amino acid sequence of peptides that can disrupt D1-D2 coupling. By "substantially identical" is meant any nucleotide sequence with similarity to the genetic sequence of a nucleic acid of the invention, or a fragment or a derivative thereof. The term "substantially identical" can also be used to describe similarity of polypeptide sequences. For example, nucleotide sequences or polypeptide sequences that are at least 70%, 75%, 80%, 85%, 90%, 92%, 95%, 96%, 98% or 99% identical to the D1 or D2 receptor coding sequence, or the encoded polypeptide, respectively, or fragments or derivatives thereof, and still retain ability to affect D1-D2 coupling are contemplated.

To determine whether a nucleic acid exhibits identity with the sequences presented herein, oligonucleotide alignment algorithms may be used, for example, but not limited to a BLAST (GenBank URL: www.ncbi.nlm.nih.gov/cgi-bin/BLAST/, using default parameters: Program: blastn; Database: nr; Expect 10; filter: default; Alignment: pairwise; Query genetic Codes: Standard(1)), BLAST2 (EMBL URL: http://www.embl-heidelberg.de/Services/index.html using default parameters: Matrix BLOSUM62; Filter: default, echofilter: on, Expect: 10, cutoff: default; Strand: both; Descriptions: 50, Alignments: 50), or FASTA, search, using default parameters. Polypeptide alignment algorithms are also available, for example, without limitation, BLAST 2 Sequences (www.ncbi.nlm.nih.gov/blast/bl2seq/bl2.html, using default parameters Program: blastp; Matrix: BLOSUM62; Open gap (11) and extension gap (1) penalties; gap x_dropoff: 50; Expect 10; Word size: 3; filter: default).

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. for at least 1 hour (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. for at least 1 hour (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, but not wishing to be limiting, stringent conditions are selected to be about 5° C. lower than the thermal melting point for the specific sequence at a defined ionic strength and pH.

By protein transduction domain it is meant a sequence of nucleic acids that encode a polypeptide, or a sequence of amino acids comprising the polypeptide, wherein the polypeptide facilitates localization to a particular site, for example a cell or the like, or it may facilitate transport across a membrane or lipid bilayer. The polypeptides and nucleic acids of the present invention may be fused to a protein transduction domain to facilitate transit across lipid bilayers or membranes. Also, the present invention contemplates that the polypeptide as described herein may be linked or attached to a support, a macromolecule, a non-protein carrier or a protein carrier optionally via a spacer compound, molecule or the like.

Many polypeptides and nucleic acids do not efficiently cross the lipid bilayer of the plasma membrane, and therefore enter into cells at a low rate. However, there are certain naturally occurring polypeptides that can transit across membranes independent of any specific transporter. Antennapedia (Drosophila), TAT (HIV) and VP22 (Herpes) are examples of such polypeptides. Fragments of these and other polypeptides have been shown to retain the capacity to transit across lipid membranes in a receptor-independent fashion. These fragments, termed protein transduction domains, are generally 10 to 27 amino acids in length, possess multiple positive charges, and in several cases have been predicted to be ampipathic. Polypeptides and nucleic acids that are normally inefficient or incapable of crossing a lipid bilayer, can be made to transit the bilayer by being fused to a protein transduction domain.

U.S. Publication 2002/0142299 (which is incorporated herein by reference) describes a fusion of TAT with human beta-glucuronidase. This fusion protein readily transits into various cell types both in vitro and in vivo. Furthermore, TAT fusion proteins have been observed to cross the blood-brain-barrier. Frankel et al. (U.S. Pat. No. 5,804,604, U.S. Pat. No. 5,747,641, U.S. Pat. No. 5,674,980, U.S. Pat. No. 5,670,617, and U.S. Pat. No. 5,652,122; which are incorporated herein by reference) have also demonstrated transport of a protein (beta-galactosidase or horseradish peroxidase) into a cell by fusing the protein with amino acids 49-57 of TAT.

PCT publication WO01/15511 (which is incorporated herein by reference) discloses a method for developing protein transduction domains using a phage display library. The method comprises incubating a target cell with a peptide display library and isolating internalized peptides from the cytoplasm and nuclei of the cells and identifying the peptides. The method further comprised linking the identified peptides to a protein and incubating the peptide-protein complex with a target cell to determine whether uptake is facilitated. Using this method a protein transduction domain for any cell or tissue type may be developed. US Publication 2004/0209797 (which is incorporated herein by reference) shows that reverse isomers of several of the peptides identified by the above can also function as protein transduction domains.

PCT Publication WO99/07728 (which is incorporated herein by reference) describes linearization of protegrin and tachyplesin, naturally occurring as a hairpin type structure held by disulphide bridges. Irreversible reduction of disulphide bridges generated peptides that could readily transit cell membranes, alone or fused to other biological molecules. US Publication 2003/0186890 (which is incorporated herein by reference) describes derivatives of protegrin and tachyplesin that were termed SynB1, SynB2, SynB3, etc. These SynB peptides were further optimized for mean hydrophobicity per residue, helical hydrophobic moment (amphipathicity), or beta hydrophobic moment. Various optimized amphipathic SynB analog peptides were shown to facilitate transfer of doxorubicin across cell membranes. Further, doxorubicin linked to a SynB analog was observed to penetrate the blood-brain-barrier at 20 times the rate of doxorubicin alone.

The protein transduction domains described in the preceding paragraphs are only a few examples of the protein transduction domains available for facilitating membrane transit of small molecules, polypeptides or nucleic acids. Other examples are transportan, W/R, AlkCWK18, DipaLytic, MGP, or RWR. Still many other examples will be recognized by persons skilled in the art A protein transduction domain and an agent of the present invention may be placed together in sufficient proximity and maintained together for a sufficient time to allow the protein transduction domain to influence pharmaceutical product performance of the agent. Contemplated associations of protein transduction domain and agent include, for example and without limitation: non-covalent associations such as electrostatic interactions, hydrogen bonding, ionic bonds or complexes, Van der Waals bonds; covalent linkages such as conventional methods of cross-linking; linkages that are activated, in vitro and/or in vivo by electromagnetic radiation; any covalent bond such as a peptide bond; any biochemical interaction known to protein biochemists, such as biotin/streptavidin, nickel/Histidine, glutathione/glutathione-S-transferase, or antigen/antibody; physical associations within matrix structures or encapsulating systems; etc.

The present invention provides an agent that may be any small molecule chemical compound, polypeptide, nucleic acid, or any combination thereof that can modulate DA receptor functionality through disruption of D1-D2 coupling. Accordingly, the present invention provides a polypeptide of about 3 to less than about 140 amino acids, preferably 7 to 109 amino acids, more preferably 15 to 100 amino acids and comprising an amino acid sequence that is at least 80% identical, for example, but not limited to 80%, 85%, 90%, 95%, 96%, 97%, 98%, 99%, or 100% identical to the sequence of $D2_{IL3\text{-}29}$ (SEQ ID NO:1), $D2L_{IL3\text{-}29\text{-}2}$ (SEQ ID NO:2), $D2_{IL3\text{-}L}$ (SEQ ID NO:3), or $D1_{CT}$ (SEQ ID NO:4). The present invention also provides a nucleic acid encoding a polypeptide of about 3 to less than about 140 amino acids, preferably about 10 to about 109 amino acids, more preferably about 15 to about 100 amino acids and comprising an amino acid sequence that is at least 80% identical, for example, but not limited to 80%, 85%, 90%, 95%, 96%, 97%, 98%, 99%, or 100% identical to the sequence of $D2_{IL3\text{-}29}$ (SEQ ID NO:1), $D2L_{IL3\text{-}29\text{-}2}$ (SEQ ID NO:2), $D2_{IL3\text{-}L}$ (SEQ ID NO:3), or $D1_{CT}$ (SEQ ID NO:4). The polypeptide or nucleic acid may optionally be fused to a protein transduction domain.

A polypeptide of the invention can be synthesized in vitro or delivered to a cell in vivo by any conventional method. As a representative example of an in vitro method, the polypeptide may be chemically synthesized in vitro, or may be enzymatically synthesized in vitro in a suitable biological expression system, such as without limitation, wheat germ extract or rabbit reticulocyte lysate. As a representative example of an in vivo method, a DNA, RNA, or DNA/RNA hybrid molecule comprising a nucleotide sequence encoding a polypeptide of the invention is introduced into an animal, and the nucleotide sequence is expressed within a cell of an animal.

The nucleotide sequence may be operably linked to regulatory elements in order to achieve preferential expression at desired times or in desired cell or tissue types. Furthermore, as will be known to one of skill in the art, other nucleotide sequences including, without limitation, 5' untranslated region, 3' untranslated regions, cap structure, poly A tail, translational initiators, sequences encoding signalling or targeting peptides, translational enhancers, transcriptional enhancers, translational terminators, transcriptional terminators, transcriptional promoters, may be operably linked with the nucleotide sequence encoding a polypeptide (see as a representative examples "Genes VII", Lewin, B. Oxford University Press (2000) or "Molecular Cloning: A Laboratory Manual", Sambrook et al., Cold Spring Harbor Laboratory, 3rd edition (2001)). A nucleotide sequence encoding a polypeptide or a fusion polypeptide comprising a polypeptide agent and a protein transduction domain may be incorporated into a suitable vector. Vectors may be commercially obtained from companies such as Stratagene or InVitrogen. Vectors can also be individually constructed or modified using standard molecular biology techniques, as outlined, for example, in Sambrook et al. (Cold Spring Harbor Laboratory, 3rd edition (2001)). A vector may contain any number of nucleotide sequences encoding desired elements that may be operably linked to a nucleotide sequence encoding a polypeptide or fusion polypeptide comprising a protein transduction domain. Such nucleotide sequences encoding desired elements, include, but are not limited to, transcriptional promoters, transcriptional enhancers, transcriptional terminators, translational initiators, translational, terminators, ribosome binding sites, 5' untranslated region, 3' untranslated regions, cap structure, poly A tail, origin of replication, detectable markers, affinity tags, signal or target peptide, Persons skilled in the art will recognize that the selection and/or construction of a suitable factor may depend upon several factors, including, without limitation, the size of the nucleic acid to be incorporated into the vector, the type of transcriptional and translational control elements desired, the level of expression desired, copy number desired, whether chromosomal integration is desired, the type of selection process that is desired, or the host cell or the host range that is intended to be transformed.

The DNA, RNA, or DNA/RNA hybrid molecule may be introduced intracellularly, extracellularly into a cavity, interstitial space, into the circulation of an organism, orally, or by any other standard route of introduction for therapeutic molecules and/or pharmaceutical compositions. Standard physical methods of introducing nucleic acids include, but are not limited to, injection of a solution comprising RNA, DNA, or RNA/DNA hybrids, bombardment by particles covered by the nucleic acid, bathing a cell or organism in a solution of the nucleic acid, or electroporation of cell membranes in the presence of the nucleic acid.

A nucleic acid may be introduced into suitable eukaryotic cells ex vivo and the cells harboring the nucleic acid can then be inserted into a desired location in an animal. A nucleic acid can also be used to transform prokaryotic cells, and the transformed prokaryotic cells can be introduced into an animal, for example, through an oral route. Those skilled in the art will recognize that a nucleic acid may be constructed in such a fashion that the transformed prokaryotic cells can express and secrete a polypeptide of the invention. Preferably, the prokaryotic cell is part of the animal's endogenous intestinal microflora. With regards to human examples of endogenous microflora are, without wishing to be limiting, *Lactobacillus acidophillus, Streptococcus thermophilus,* and *Bifidobacte-* rium bifidum. A nucleic acid may also be inserted into a viral vector and packaged into viral particles for efficient delivery and expression.

Dosage Forms

An agent of the present invention, for example, D1 or D2 polypeptides or nucleic acids encoding these polypeptides or antibodies or small molecules capable of disrupting D1-D2 coupling, may be formulated into any convenient dosage form. The dosage form may comprise, but is not limited to an oral dosage form wherein the agent is dissolved, suspended or the like in a suitable excipient such as but not limited to water. In addition, the agent may be formulated into a dosage form that could be applied topically or could be administered by inhaler, or by injection either subcutaneously, into organs, or into circulation. An injectable dosage form may include other carriers that may function to enhance the activity of the agent. Any suitable carrier known in the art may be used. Also, the agent may be formulated for use in the production of a medicament. Many methods for the productions of dosage forms, medicaments, or pharmaceutical compositions are well known in the art and can be readily applied to the present invention by persons skilled in the art.

Combination therapy with agents of the present invention or other agents useful for preventing and/or treating neurological diseases or disorders is contemplated. With regards to combination therapy suitable dosage forms again include capsules, tablets, and the like, preferably for oral administration, although any dosage form, for any route of administration is contemplated. Combination therapy can be administered as separate entities, e.g. two tablets or other forms, each containing one agent, or may be administered as a single dosage form containing both drugs, or concomitant use.

In case of oral administration of two or more different agents, the single dose can be, but is not limited to a capsule, tablet, or oral solution, and it may also contain inactive component(s) that is necessary to form the single delivery system.

Combination therapy medications of the present invention may be administered by any desired route, for example without limitation, administration can be transdermal (patch), buccal, sublingual, topical, nasal, parenteral (subcutaneous, intramuscular, intravenous, intradermal,), rectal, vaginal, administration. Various combinations of controlled release/rapid release are also contemplated.

Treatment

The methods and compounds of the present invention are useful for preventing and/or treating diseases that are characterized by abnormal levels of D1-D2 interaction or complex formation. The following are some non-limiting examples of such diseases: depression, including major depressive illness and depression in bipolar disorder, and psychiatric conditions that require treatment with antipsychotic medication, including schizophrenia, psychosis in bipolar disorder, stimulant drug intoxication, delirium, Tourette's syndrome, anxiety or a combination thereof.

Neurological, Neuropsychiatric Diseases

Depression is characterized by profound sadness, pronounced changes in sleep, appetite, and energy. Recurrent thoughts of death or suicide, persistent physical symptoms that do not respond to treatment, such as headaches, digestive disorders, and chronic pain are some symptoms of major depression. Major depression is a unipolar depression, while bipolar disorder (manic depression) involves both depression and mania. Early identification and treatment of depression is required to minimize risk of suicide and self-inflicted injury. The method and compounds of the present invention are useful in decreasing D1-D2 coupling and may be used for preventing and/or treating depression.

Accordingly the present invention provides methods for modulating DA functionality by disrupting D1-D2 coupling in a mammal. Any mammal including, without limitation, human, rat, cow, pig, dog, or mouse, may be treated with the agents and methods of the present invention.

The present invention will be further illustrated in the following examples.

EXPERIMENTS

Experiment 1

D1-D2 Receptor Complex is Facilitated by the D1R Carboxyl Tail (CT) and the Third Intracellular Loop (IL3) of D2R To confirm previous reports of a D1-D2 receptor complex we used rat striata in co-immunoprecipitation (co-IP) experiments. As shown in FIG. 1A, the D1R was able to co-precipitate with the D2R, confirming the presence of a D1-D2 receptor complex. In an attempt to define the structural basis for the observed D1-D2 coupling, we carried out affinity purification using GST (glutathione-S-transferase)-fusion proteins encoding the $D1_{CT}$ and the third intracellular loop ($D1_{IL3}$), since both $D1_{CT}$: $A_{332}$-$T_{446}$ and $D1_{IL3}$: $R_{219}$-$K_{272}$ contain putative consensus sequences for receptor phosphorylation, desensitization and potential binding sites for various proteins important for signalling (e.g. G proteins, NMDA receptor NR1, NR2A subunits)[81-82]. As shown in FIG. 1B, GST-$D1_{CT}$, but not GST-$D1_{IL3}$ or GST alone, precipitated solubilized striatal D2R as illustrated by the D2 antibody immunolabeled Western blot, indicating that the D1R can interact with D2R through the $D1_{CT}$ region. To locate the interacting site on D2R, GST-fusion proteins encoding IL3 from both the D2 short (D2S) and D2 Long (D2L) (GST-$D2_{IL3-L}$: $K_{211}$-$Q_{373}$, GST-$D2_{IL3-S}$: $K_{211}$-$Q_{315}$) were used in affinity purification assays. As shown in FIG. 1C, GST-$D2_{IL3-L}$, but not GST-$D2_{IL3-S}$ or GST alone was able to pull-down D1 receptors. Since the D2L and D2S are differentiated by the additional 29 amino-acid within the third intracellular loop, the fact that only D2L but not D2S interacts with D1R made us suspect that this specific 29 amino-acid may contain the D1-D2 interacting site. The affinity "pull down" results revealed that the sequence encoded by the $D2_{IL3-29}$ facilitates the interaction between D1 and D2 receptors since only the GST-$D2_{IL3-L}$ and GST-$D2_{IL3-29}$: $G_{242}$-$V_{270}$ but not GST-$D2_{IL3-S}$, GST-$D2_{CT}$: $T_{399}$-$C_{414}$ or GST alone was able to pull-down D1 receptors (FIG. 1D). Further experiments using fragments of $D2_{IL3-29}$ show that GST-$D2L_{IL3-29-2}$: $I_{256}$-$V_{270}$, but not the GST-$D2L_{IL3-29-1}$: $G_{242}$-$V_{255}$ or GST, can successfully pull-down D1R from solubilized rat striatum (FIG. 1E). Furthermore, in vitro binding assay suggested direct interaction between D1R and D2R (FIG. 1F). These results provide evidence that the D1-D2 direct interaction is dependent on sequences located in the $I_{256}$-$V_{270}$ region of D2R. Further, as shown in FIG. 1G, pre-incubation of GST-D2-IL3-29-2 inhibits the D1-D2 interaction as indexed by the co-immunoprecipitation in a concentration dependent manner.

Experiment 2

Figure 2:
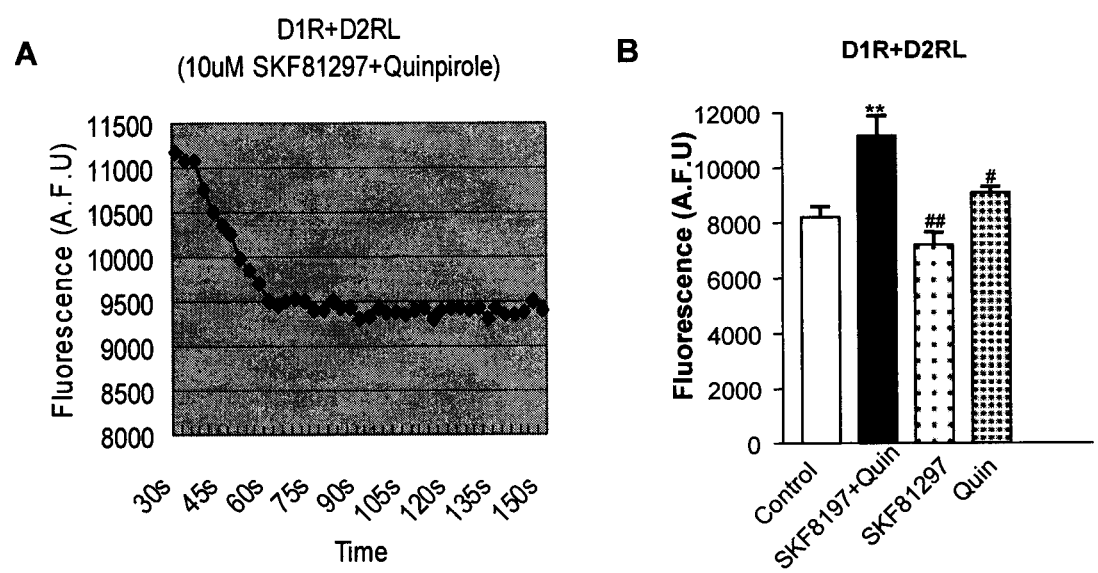
Figure 3:
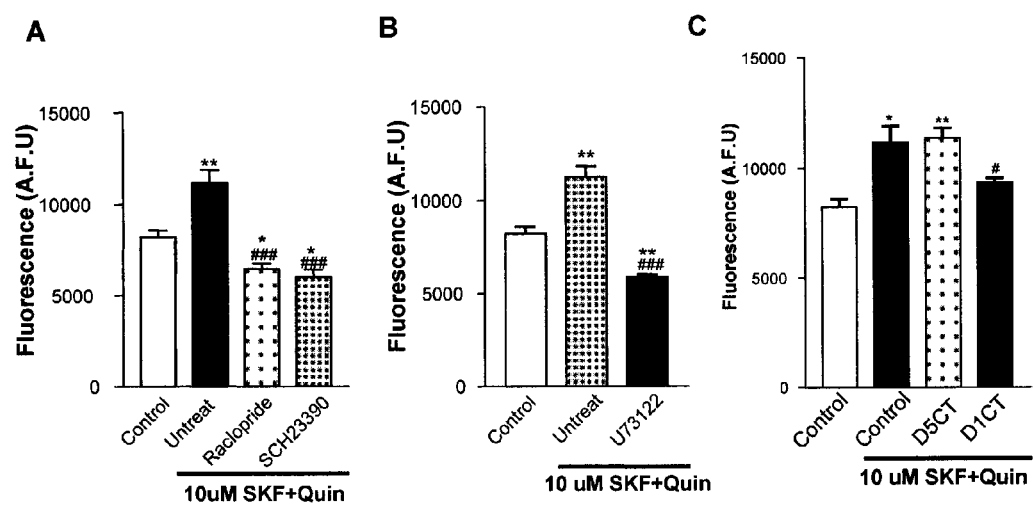

Co-Activation of the D1-D2 Receptor Induces an Increase in Intracellular $Ca^{2+}$ Mediated by Phospholipase C Activation To investigate the functional implication of the D1-D2 coupling, we examined the ability of this complex to promote Gq/11 signaling as indexed by changes in intracellular $Ca^{2+}$ levels[83-85]. In HEK-293T cells co-transfected with D1R and D2R we examined changes in intracellular $Ca^{2+}$ levels when co-treated with 10 μM SKF81297 and 10 μM quinpirole. Cells that were treated with both agonists exhibited a rapid and significant increase in intracellular $Ca^{2+}$ levels that peaked 30 seconds after addition of agonists (FIG. 2A). However, cells treated with either SKF81297 or quinpirole alone had no change in $Ca^{2+}$ levels when compared to nontreated control cells (FIG. 2B). The increase in $Ca^{2+}$ levels could be blocked by pretreatment with either 10 μM raclopride (D2 antagonist) or 10 μM SCH23390 (D1 antagonist), as shown in FIG. 3A. Furthermore, this unique D1-D2 co-activation dependent signaling is mediated by phospholipase C (PLC) activation, since pretreatment with the PLC inhibitor U73122 (10 μM) inhibited the increase in $Ca^{2+}$ levels induced by co-activation of D1R and D2R (FIG. 3B). These data are in line with previous studies showing that this signaling likely recruits Gq/11 upon co-activation of DA receptors, leading to downstream activation of PLC[83-85].

Experiment 3

Disruption of D1-D2 Coupling Abolished the D1-D2 Co-Activation Induced Increases in Intracellular $Ca^{2+}$ Our preliminary data has shown that coexpression of the $GST-D1_{CT}$ is able to affinity pull down the D2R (FIG. 1B). Thus, to test whether D1-D2 coupling is necessary for the D1-D2 co-activation induced increases in intracellular $Ca^{2+}$, we examined changes in intracellular $Ca^{2+}$ levels when co-treated with 10 μM SKF81297 and 10 μM quinpirole in HEK-293T cells cotransfected with mini-genes encoding $D1_{CT}$, $D5_{CT}$ along with D1R and D2R. As shown in FIG. 3C, coexpression of the $D1_{CT}$ mini-gene but not the $D5_{CT}$ mini-gene abolished D1-D2 co-activation induced increases in intracellular $Ca^{2+}$ suggesting that the D1-D2 coupling may be responsible for the observed increases in intracellular $Ca^{2+}$ induced by D1/D2 co-activation.

Experiment 4

D1-D2 Coupling is Upregulated in Post-Mortem Brain Tissue of Depression Patients Both D1R and D2R have been implicated in the pathology of psychiatric diseases such as schizophrenia. To test whether D1-D2 coupling is altered in disease, we carried out co-immunoprecipitation experiments in a double-blind manner on 60 post-mortem brain striatum samples from the Stanley Foundation, which includes 15 samples from each of four groups: control, schizophrenia, bipolar and severe depression. The four groups were matched by age, sex, race, post-mortem interval, pH, side of brain, and mRNA quality by the Stanley Foundation brain bank. The same amount of protein from each sample was incubated with anti-D2 receptor antibody and protein A/G agarose. The precipitated proteins were divided equally into two groups before being subjected to SDS-PAGE and immunoblotted with either D1 antibody or D2 antibody. Each Western blot included 3 samples from each group and the intensity of each protein band was quantified by densitometry (software: AIS from Imaging Research Inc). Each sample is presented as the percentage of the mean of three control samples on the same blot. As shown in FIG. 4A, the co-immunoprecipitation of D1 by the D2 receptor antibody was significantly enhanced in the depression post-mortem brain samples compared to control brains. The levels of directly immunoprecipitated D2 receptors were not significantly different between the control and depression groups (data not shown). Therefore, the observed D1-D2 coupling upregulation seen in the depression brain samples may be a primary aspect of depression pathophysiology. However, we are aware that two issues may have influenced the results: (i) we do not have the patient history of antidepressant usage, and (ii) that some of the depression patients had history of drug abuse (5 out of 15) and/or alcohol abuse (10 out of 15), which may account for the large standard error in our results. Given the complex nature of data involving human brain tissue, we have confirmed the D1-D2 coupling is enhanced in rats with depressive-like behaviours induced by three different uncontrollable stress paradigms.

Experiment 5

Chronic Antidepressant Treatment Leads to a Decrease in the D1-D2 Coupling

Figure 5:
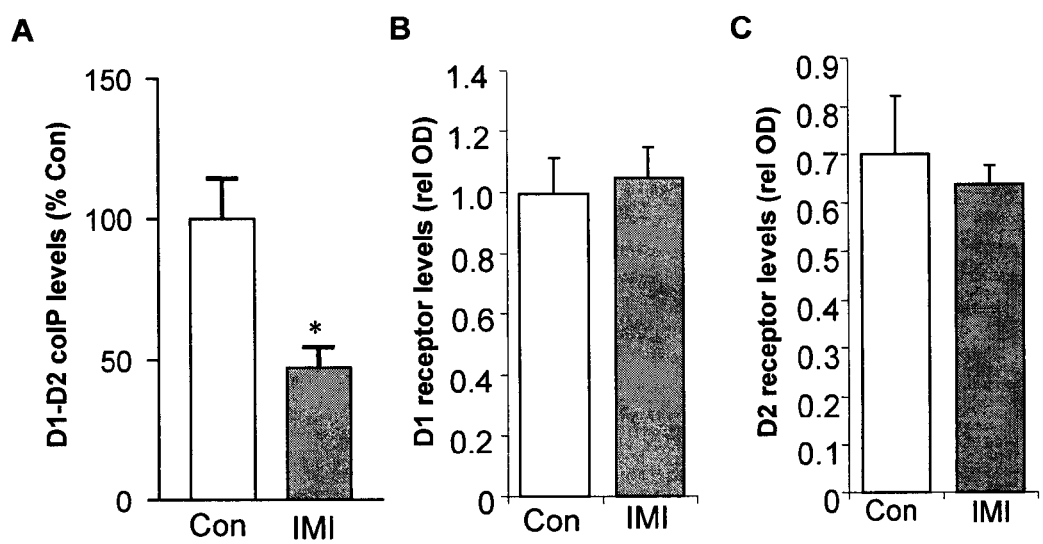

If the observed increases in the D1-D2 coupling in the postmortem brain tissue of depression patients were indeed part of the pathological foundation of depression, one would imagine that chronic antidepressant treatment might correct such a change in the D1-D2 coupling. To test this hypothesis, we injected rats subcutaneously with 10 mg/kg/day of imipramine, a TCA, for a period of 14 days. On the 14th day, rats were sacrificed, striata dissected and were processed for co-IP assays and Western blots. Co-immunoprecipitation experiments revealed that chronic antidepressant treatment led to a decrease in D1-D2 coupling (FIG. 5A). Furthermore, this decrease in the D1-D2 coupling could not be attributed to changes in receptor levels, since Western blots revealed no significant change in D1R and D2R levels when comparing chronically treated rats with control rats (FIG. 5B,C).

Experiment 6

D1-D2 Coupling is Up-Regulated in Animals with Depressive-Like Behaviours

Figure 6:
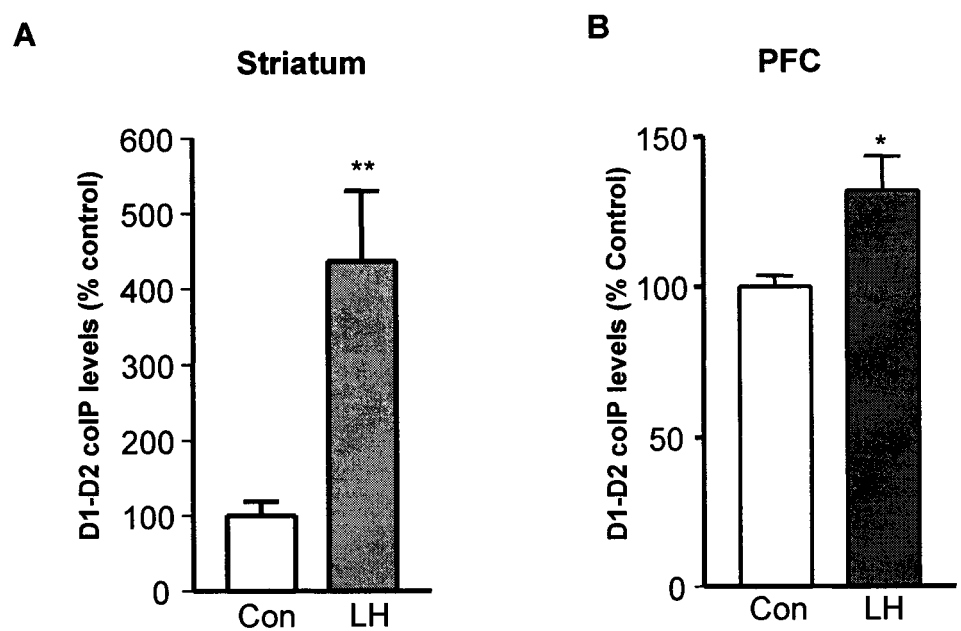
Figure 7:
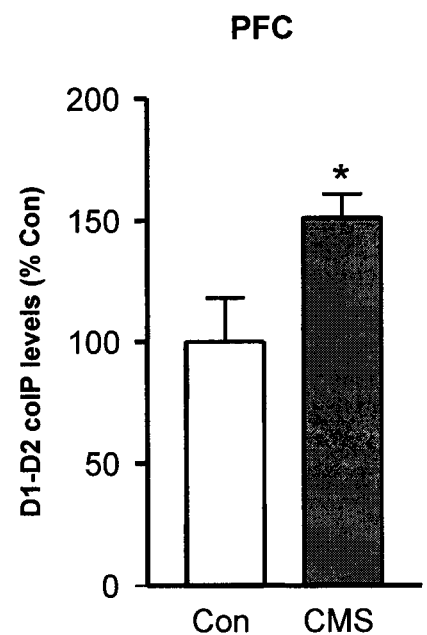

This was tested by co-immunoprecipitation of the D1R by the D2R primary antibody from solubilized proteins extracted from striatum, PFC of rats from the two animal models with depressive-like behaviours compared to the control groups. Briefly, anti-D2 antibody is incubated with solubilized protein for 4 hours followed by the addition of protein A/G beads. Incubation with protein A/G beads continues overnight followed by high stringency washes. The immunoprecipitated proteins are eluted from the beads and subjected to SDS-PAGE for Western blot analysis. Control experiments without D2 antibody are carried out concurrently. The co-immunoprecipitated proteins were immunoblotted with the D1, antibody and the intensity of each protein band was quantified by densitometry. Each co-immunoprecipitation is in parallel with western blot analysis of the initial levels of solubilized protein and directly immunoprecipitated proteins. As shown in FIG. 6, 7, striata (LH model) and PFC from rats (LH model and CMS model) showed a significant increase in the D1-D2 coupling compared to control rats (n=5 p<0.05). Furthermore, there was no significant change in D1R or D2R protein levels (data not shown).

Experiment 7

Animal Model #1: Learned Helplessness Induced by Inescapable Shock

The learned helplessness procedure consists of two separate stress sessions. On day 1, animals are placed in soundattenuated operant boxes (Med Associates, St. Albans, Vt.) where they receive inescapable shock, with lights off and no levers present. Shock is delivered as a scrambled pulsed 0.8 mA current through metal floor bars. Both shock duration and intertrial intervals are randomly varied (1.5-60 sec and 1-30 sec, respectively), for a total shock exposure of 25 min. On day 2 rats are placed in the operant boxes, and given exactly 15 trials of escapable shock, each lasting for a maximum 60 sec, with a fixed intertrial interval of 24 seconds. Initiation of shock (0.8 mA) is accompanied by the onset of a red cue light placed directly above a lever which when pressed terminates the shock and turns off the cue light. A houselight outside the immediate chamber is kept on during the entire trial. A bar press within the first 20 seconds of shock initiation is recorded as an escape response. A response between 20-60 seconds is classified as failure to escape. After 60 seconds the shock is automatically terminated and the trial counted as a failure. Escape performance and latency to escape are recorded for each animal over the 15 trials. Animals are classified as learned helpless (LH) if they fail to escape in 10 or more of the 15 trials. Rats that fail to escape in 5 or less of the 15 trials are termed resistant or non-learned helpless (nLH)[86-87]. Animals that fail 5-10 times are considered borderline. In addition to home cage controls, another group may be placed in the boxes in day 1 without receiving any shock. On day 2 this group receives escapable shock. It serves as a behavioral control only, by demonstrating that control rats can learn to escape during the 15 trials. For each treatment condition, 8 LH, 8 nLH and 8 cage controls are sacrificed 24 hr after the escapable shock session via decapitation. Brains are quickly dissected and frozen on dry ice. All samples are kept at −80° C. for biochemistry and pharmacology analysis.

Experiment 8

Animal Model #2: Chronic Mild Stress

Rats are first trained to drink a 1% sucrose solution, by exposing them to sucrose in place of water for 48 h. They then receive a series of sucrose preference tests, preceded by 23 h food and water deprivation, where each animal is presented simultaneously with 2 bottles, one containing 1% sucrose the other water. The position of the 2 bottles (right/left) is varied randomly from trial to trial and, within each trial, is counterbalanced across the animals in each group. During the test, both bottles are removed after 30 min for weighing, and replaced by a second pair of preweighed bottles (with the positions of the 2 bottles reversed), which are removed and weighed at 60 min. Tests are timetabled at the start of the dark cycle (1800-1900 h) for half of the animals and in the first half of the light cycle (1000-1100 h) for the other half. Following the final baseline test, each group of animals will be divided into 2 subgroups, matched on the basis of their total (60-min) sucrose intake in the final baseline test. One pair of subgroups will be exposed to CMS for 6 weeks; the control subgroups will not be stressed, other than the food/water deprivation that precedes each sucrose preference test. In each of the first four weeks, the CMS schedule (adopted from ref. 88) will consist of the following elements: Tues. 1900-Wed. 1000 h Paired housing (new partner); Wed. 1000-1800 h Stroboscopic illumination (in dark); Wed. 1800-Thurs. 1000 h Food deprivation in soiled cage (water in sawdust); Thurs. 1000-1800 h 45° cage tilt; Thurs. 1800-Fri. 1000 h Mouse cage; Fri. 1000-1800 h Paired housing (new partner); Fri. 1800-Sat. 1000 h Water deprivation; Sat. 1000-1800 h Stroboscopic illumination (in dark); Sat. 1800-Sun. 0600 h Light on; Sun. 0600-1800 h Intermittent lighting (off/on every 2 h); Mon. 1100 or 1900 h 23-h food and water deprivation; Tue. 1000 or 1800 h 1-h sucrose intake test. In the final two weeks, the CMS timetable will be rearranged, with paired housing (Mon. night) and food/water deprivation (Tues. night) immediately before sucrose intake test. Body weight will be monitored daily. After the last sucrose preference test, animals will be left undisturbed until next morning during when they will be decapitated.

Experiment 9

Increase in the D1-D2 Coupling in Rats Subjected to Forced-Swim Tests (FST)

Figure 8:
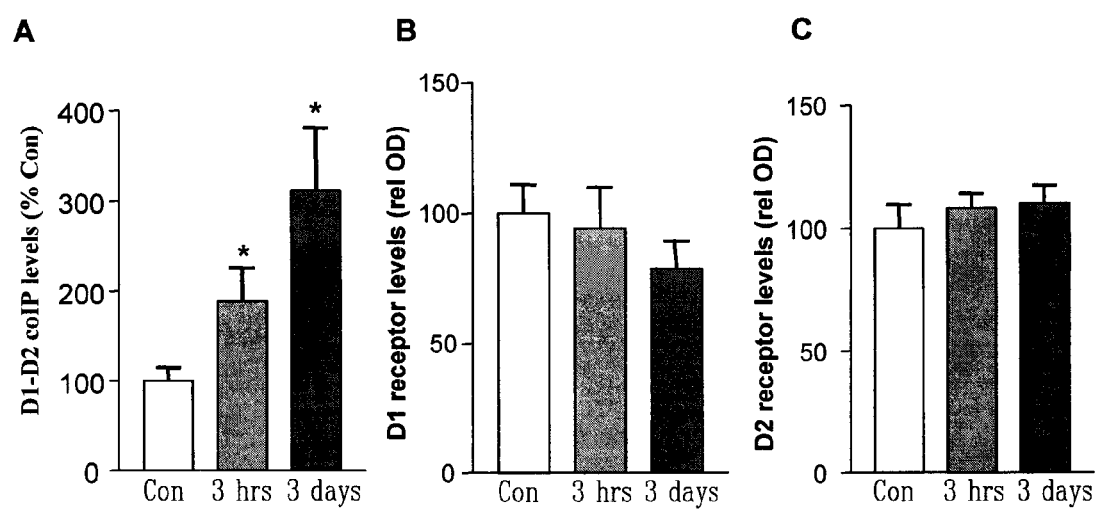

To investigate the possibility that the D1-D2 coupling plays a role in the pathology of depression, we examined the D1-D2 coupling using D1R antibody to co-IP the D2R from striata of rats subjected to FST. The FST (or behavioural despair) is a good model to test for the efficacy of antidepressant drugs. As shown in FIG. 8A, Striata from rats sacrificed 3 hours or 3 days after the last FST trial exhibited a significant increase in the D1-D2 coupling compared to control rats. Furthermore, there was no change in D1R or D2R protein levels that could account for the increase in the D1-D2 complex formation (FIG. 8B, C). Surprisingly, rats sacrificed 3 days after the last FST trial exhibited a larger increase in the D1-D2 coupling compared to rats sacrificed 3 hours after the last FST trial and suggested long-term changes occur after FST trials.

Experiment 10

Disruption of the D1-D2 Protein Complex in Schizophrenic Brain Tissue

Figure 4:
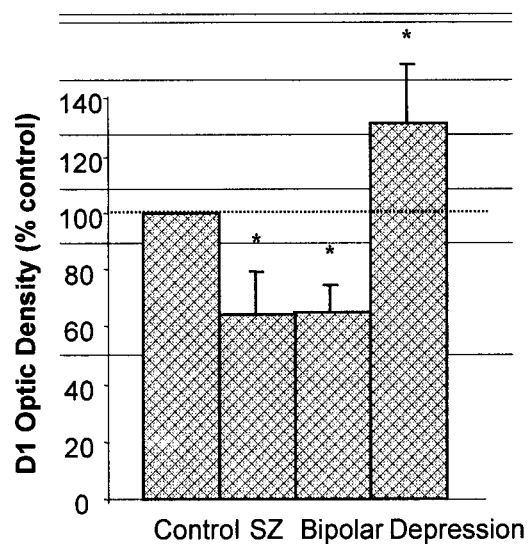
Figure 9:
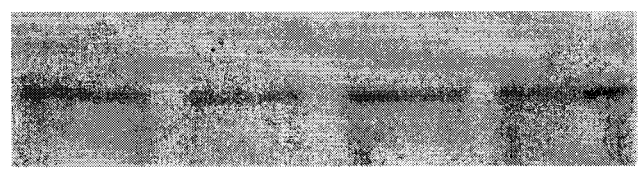
Figure 9:
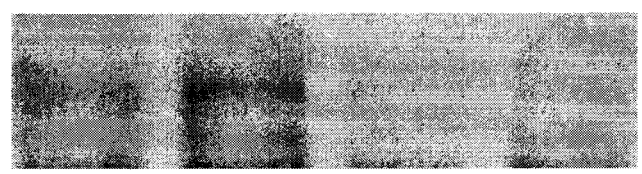

To identify the physiological relevance for the D1-D2 receptor complex formation and specifically the effect of the antipsychotic medication, we carried out co-immunoprecipitation experiments in a double-blind manner with 60 postmortem brain striatum samples from the Stanley Foundation, which includes 15 samples from each of the four groups: control, schizophrenia, bipolar and severe depression. The four groups were matched by age, sex, race, postmortem interval, pH, side of brain, and mRNA quality by the brain bank. The same amount of protein from each sample was co-immunoprecipitated with D2 receptor antibody. The precipitated proteins were divided equally into two groups and immunoblotted with either D1 antibody or D2 antibody. Consistent with our hypothesis, the co-immunoprecipitated D1 by the D2 antibody was significantly decreased in the postmortem brain samples from both schizophrenia and bipolar patients compared to control group (FIG. 4). The levels of directly immunoprecipitated D2 were not significantly different among the four groups (data not shown). Interestingly, all the schizophrenia samples and 12 out of 15 of bipolar samples were from patients treated with antipsychotics, indicating that the observed D2-D1 interaction deficit seen in schizophrenia patients may not be a primary aspect of schizophrenia pathophysiology, it may actually reflect the pharmacological effects of antipsychotics/D2 antagonists. Thus, we further tested the D1-D2 protein complex formation in rats chronically treated with haloperidol, a clinical antipsychotic as well as a D2 antagonist (By pump 0.25 mg/kg/day for 2 weeks, to get continuous clinical occupancy[89]). As shown in FIG. 9, while the direct immunoprecipitated D2 receptors remain unchanged (top panel), the D1-D2 receptor complex formation is significantly decreased in rat with chronic antipsychotic treatment (bottom panel), suggesting that antagonizing D2 function disrupts D1-D2 receptor coupling.

Experiment 11

Figure 10:
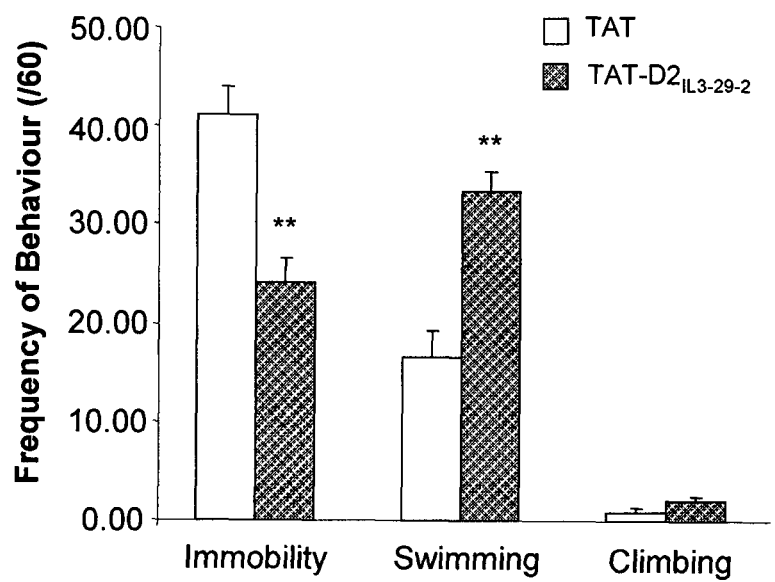

Interfering Protein Peptide that is Able to Disrupt the D1-D2 Coupling Exerts Antidepressant Effect in the Forced-Swim Test The FST is a stress model commonly used to test for the efficacy of antidepressant drugs. Thus we will examine the effect of the interfering TAT peptides on rats using the FST, developed by Porsolt and colleagues[146]. Phase 1 of the FST consists of a preconditioning period in which rats are forced to swim in an enclosed container of water (height of container, 40 cm; diameter of container, 20 cm; depth of water, 13 cm; temperature, 25° C.) for 15 min without a way to escape. In this predicament, rats will respond by becoming immobile. Twenty-four hours after being removed from the container, each rat will be returned to the water for a 5 min test (phase 2), and the behavior will be recorded by a video camera from the side of the cylinder. Rat's behavior will be classified for each 5 seconds and assigned to different categories according to the standard described previously[90] (climbing, diving, swimming, immobility and latency to immobility) from videotapes by a trained observer who is blinded to the experimental conditions). To examine the potential antidepressant effect of the interfering peptide, TAT-D2L$_{IL3-29-2}$ (5 pmol) and TAT alone peptide were given ICV three times similar to antidepressant drugs: 1 hr and 5 hrs after the pre-swim trial (phase 1) respectively and 1 hour before the swim test (phase 2). As shown in FIG. 10, Intra-PFC administration of TAT-D2L$_{IL3-29-2}$, but not TAT alone, decreased the frequencies of rat immobility and increased the frequencies of rat swimming and climbing behaviors in a 5 mins forced swimming test. Each value is the mean±S.E.M. for a group of 6 rats. Data were analyzed by one-way analysis of variance (ANOVA).

One or more currently preferred embodiments have been described by way of example. It will be apparent to persons skilled in the art that a number of variations and modifications can be made without departing from the scope of the invention as defined in the claims.

REFERENCES

1. Missale, C., S. R. Nash, S. W. Robinson, M. Jaber, and M. G. Caron, (1998) *Dopamine receptors: from structure to function*. Physiol Rev. 78(1): 189-225.
2. Picetti, R., A. Saiardi, T. Abdel Samad, Y. Bozzi, J. H. Baik, and E. Borrelli, (1997) *Dopamine D2 receptors in signal transduction and behavior*. Crit Rev Neurobiol. 11(2-3): 121-42.
3. Park, S. K., M. D. Nguyen, A. Fischer, et al., (2005) *Par-4 links dopamine signaling and depression*. Cell. 122(2): 275-87.
4. *Canadian Community Health Survey Mental Health and Well-being* 2002.
5. Dewa, C. S., P. Goering, and E. Lin, (2000) *Bridging the worlds of academia and business: exploring the burden of mental illness in the workplace*. The Economics of Neuroscience. 2(6): 47-9.
6. Stephens, T. and N. Joubert, (2001) *The economic burden of mental health problems in Canada*. Chronic Dis Can. 22(1): 18-23.
7. Baldessarini, R. J., (2006), *Drug therapy of depression and anxiety disorders*, in *Goodman & Gilman's The Pharmacological Basis of Therapeutics*, L. L. Brunton, Editor. McGraw-Hill.
8. Nestler, E. J., M. Barrot, R. J. DiLeone, A. J. Eisch, S. J. Gold, and L. M. Monteggia, (2002) *Neurobiology of depression*. Neuron. 34(1): 13-25.
9. Vaidya, V. A. and R. S. Duman, (2001) *Depresssion—emerging insights from neurobiology*. Br Med Bull. 57: 61-79.
10. Beninger, R. J. and R. Miller, (1998) *Dopamine D1-like receptors and reward-related incentive learning*. Neurosci Biobehav Rev. 22(2): 335-45.
11. Hagan, J. J., D. N. Middlemiss, P. C. Sharpe, and G. H. Poste, (1997) *Parkinson's disease: prospects for improved drug therapy*. Trends Pharmacol Sci. 18(5): 156-63.
12. Hollerman, J. R., L. Tremblay, and W. Schultz, (1998) *Influence of reward expectation on behavior-related neuronal activity in primate striatum*. J Neurophysiol. 80(2): 947-63.
13. Iversen, S. D., (1995) *Interactions between excitatory amino acids and dopamine systems in the forebrain: implications for schizophrenia and Parkinson's disease*. Behav Pharmacol. 6(5 And 6): 478-491.
14. Schultz, W., (1997) *Dopamine neurons and their role in reward mechanisms*. Curr Opin Neurobiol. 7(2): 191-7.
15. Watanabe, M., T. Kodama, and K. Hikosaka, (1997) *Increase of extracellular dopamine in primate prefrontal cortex during a working memory task*. J Neurophysiol. 78(5): 2795-8.
16. Tremblay, L. K., C. A. Naranjo, L. Cardenas, N. Herrmann, and U. E. Busto, (2002) *Probing brain reward system function in major depressive disorder: altered response to dextroamphetamine*. Arch Gen Psychiatry. 59(5): 409-16.
17. Kapur, S. and J. J. Mann, (1992) *Role of the dopaminergic system in depression*. Biol Psychiatry. 32(1): 1-17.
18. Anisman, H., J. Irwin, and L. S. Sklar, (1979) *Deficits of escape performance following catecholamine depletion: implications for behavioral deficits induced by uncontrollable stress*. Psychopharmacology (Berl). 64(2): 163-70.
19. Anisman, H., G. Remington, and L. S. Sklar, (1979) *Effect of inescapable shock on subsequent escape performance: catecholaminergic and cholinergic mediation of response initiation and maintenance*. Psychopharmacology (Berl). 61(2): 107-24.
20. D'Aquila, P. S., M. Collu, G. L. Gessa, and G. Serra, (2000) *The role of dopamine in the mechanism of action of antidepressant drugs*. Eur J Pharmacol. 405(1-3): 365-73.
21. Basso, A. M., K. B. Gallagher, N. A. Bratcher, et al., (2005) *Antidepressant-like effect of D(2/3) receptor-, but not D(4) receptor-activation in the rat forced swim test*. Neuropsychopharmacology. 30(7): 1257-68.
22. Cervo, L., G. Grignaschi, and R. Samanin, (1990) *The role of the mesolimbic dopaminergic system in the desipramine effect in the forced swimming test*. Eur J. Pharmacol. 178 (1): 129-33.
23. Gambarana, C., O. Ghiglieri, I. Taddei, A. Tagliamonte, and M. G. De Montis, (1995) *Imipramine and fluoxetine prevent the stress-induced escape deficits in rats through a distinct mechanism of action*. Behav Pharmacol. 6(1): 66-73.
24. Hirano, S., S. Miyata, K. Onodera, and J. Kamei, (2007) *Involvement of dopamine D1 receptors and alpha1-adrenoceptors in the antidepressant-like effect of chlorpheniramine in the mouse tail suspension test*. Eur J Pharmacol. 562(1-2): 72-6.
25. Muscat, R., D. Sampson, and P. Willner, (1990) *Dopaminergic mechanism of imipramine action in an animal model of depression*. Biol Psychiatry. 28(3): 223-30.

26. Nikulina, E. M., J. A. Skrinskaya, and N. K. Popova, (1991) *Role of genotype and dopamine receptors in behaviour of inbred mice in a forced swimming test.* Psychopharmacology (Berl). 105(4): 525-9.
27. Renard, C. E., A. J. Fiocco, F. Clenet, M. Hascoet, and M. Bourin, (2001) *Is dopamine implicated in the antidepressant-like effects of selective serotonin reuptake inhibitors in the mouse forced swimming test?* Psychopharmacology (Berl). 159(1): 42-50.
28. Rogoz, Z. and G. Skuza, (2006) *Mechanism of synergistic action following co-treatment with pramipexole and fluoxetine or sertraline in the forced swimming test in rats.* Pharmacol Rep. 58(4): 493-500.
29. Sampson, D., P. Willner, and R. Muscat, (1991) *Reversal of antidepressant action by dopamine antagonists in an animal model of depression.* Psychopharmacology (Berl). 104(4): 491-5.
30. Vaugeois, J. M., D. Pouhe, F. Zuccaro, and J. Costentin, (1996) *Indirect dopamine agonists effects on despair test: dissociation from hyperactivity.* Pharmacol Biochem Behav. 54(1): 235-9.
31. Wang, W. F., Y. P. Lei, T. Tseng, W. Y. Hsu, C. F. Wang, C. C. Hsu, and Y. J. Ho, (2007) *Effects of apomorphine on the expression of learned helplessness behavior.* Chin J. Physiol. 50(2): 63-8.
32. Yamada, J., Y. Sugimoto, and S. Yamada, (2004) *Involvement of dopamine receptors in the anti-immobility effects of dopamine re-uptake inhibitors in the forced swimming test.* Eur J Pharmacol. 504(3): 207-11.
33. Learned-Coughlin, S. M., M. Bergstrom, I. Savitcheva, J. Ascher, V. D. Schmith, and B. Langstrom, (2003) *In vivo activity of bupropion at the human dopamine transporter as measured by positron emission tomography.* Biol Psychiatry. 54(8): 800-5.
34. Meyer, J. H., V. S. Goulding, A. A. Wilson, D. Hussey, B. K. Christensen, and S. Houle, (2002) *Bupropion occupancy of the dopamine transporter is low during clinical treatment.* Psychopharmacology (Berl). 163(1): 102-5.
35. Corrigan, M. H., A. Q. Denahan, C. E. Wright, R. J. Ragual, and D. L. Evans, (2000) *Comparison of pramipexole, fluoxetine, and placebo in patients with major depression.* Depress Anxiety. 11(2): 58-65.
36. Goldberg, J. F., M. A. Frye, and R. T. Dunn, (1999) *Pramipexole in refractory bipolar depression.* Am J. Psychiatry. 156(5): 798.
37. Perugi, G., C. Toni, G. Ruffolo, F. Frare, and H. Akiskal, (2001) *Adjunctive dopamine agonists in treatment-resistant bipolar II depression: an open case series.* Pharmacopsychiatry. 34(4): 137-41.
38. Post, R. M., R. H. Gerner, J. S. Carman, J. C. Gillin, D. C. Jimerson, F. K. Goodwin, and W. E. Bunney, Jr., (1978) *Effects of a dopamine agonist piribedil in depressed patients: relationship of pretreatment homovanillic acid to antidepressant response.* Arch Gen Psychiatry. 35(5): 609-15.
39. Sitland-Marken, P. A., B. G. Wells, J. H. Froemming, C. C. Chu, and C. S. Brown, (1990) *Psychiatric applications of bromocriptine therapy.* J Clin Psychiatry. 51(2): 68-82.
40. D'Haenen H, A. and A. Bossuyt, (1994) *Dopamine D2 receptors in depression measured with single photon emission computed tomography.* Biol Psychiatry. 35(2): 128-32.
41. Ebert, D., H. Feistel, T. Loew, and A. Pirner, (1996) *Dopamine and depression—striatal dopamine D2 receptor SPECT before and after antidepressant therapy.* Psychopharmacology (Berl). 126(1): 91-4.
42. Klimke, A., R. Larisch, A. Janz, H. Vosberg, H. W. Muller-Gartner, and W. Gaebel, (1999) *Dopamine D2 receptor binding before and after treatment of major depression measured by [123I]IBZM SPECT.* Psychiatry Res. 90(2): 91-101.
43. Parsey, R. V., M. A. Oquendo, Y. Zea-Ponce, et al., (2001) *Dopamine D(2) receptor availability and amphetamine-induced dopamine release in unipolar depression.* Biol Psychiatry. 50(5): 313-22.
44. Shah, P. J., A. D. Ogilvie, G. M. Goodwin, and K. P. Ebmeier, (1997) *Clinical and psychometric correlates of dopamine D2 binding in depression.* Psychol Med. 27(6): 1247-56.
45. Marinelli, M. and P. V. Piazza, (2002) *Interaction between glucocorticoid hormones, stress and psychostimulant drugs.* Eur J. Neurosci. 16(3): 387-94.
46. Oswald, L. M., D. F. Wong, M. McCaul, et al., (2005) *Relationships among ventral striatal dopamine release, cortisol secretion, and subjective responses to amphetamine.* Neuropsychopharmacology. 30(4): 821-32.
47. Steinbush, H. W. M., (1984), *Serotonin-immunoreactive neurons and their projections ni the CNS: classical transmitters and transmitter receptors in the CNS, part II*, in *Handbook of Chemical Neuroanatomy*, A. Bjorklun, T. Hokfelt, and M. J. Kuhar, Editors. Elsevier. 68-125.
48. Gerson, S. C. and R. J. Baldessarini, (1980) *Motor effects of serotonin in the central nervous system.* Life Sci. 27(16): 1435-51.
49. Prisco, S., S. Pagannone, and E. Esposito, (1994) *Serotonin-dopamine interaction in the rat ventral tegmental area: an electrophysiological study in vivo.* J Pharmacol Exp Ther. 271(1): 83-90.
50. Andreasen N C Pieces of the schizophrenia puzzle fall into place. *Science* 275: 1587-1593 [1997].
51. Flaum M & Schultz, S. K. The core symptoms of schizophrenia. *Ann. of Med.* 28: 525-531 [1996].
52. Hietala, J., and Syvalahti, E. (1996) Dopamine in schizophrenia. *Ann Med* 28(6), 557-61.
53. Seeman, P. & Lee, T. Antipsychotic drugs: direct correlation between clinical potency and presynaptic action on dopamine neurons. Science 188, 1217-9 (1975).
54. Creese, I., Burt, D. R. & Snyder, S. H. Dopamine receptor binding predicts clinical and pharmacological potencies of antischizophrenic drugs. Science 192, 481-3 (1976).
55. Kapur, S. & Mamo, D. Half a century of antipsychotics and still a central role for dopamine D2 receptors. Prog. Neuro. Biol. Psy. 27: 1081-1090 (2003).
56. Davis, K. L., Kahn, R. S., Ko, G. & Davidson, M. Dopamine in schizophrenia: a review and reconceptualization. Am J Psychiatry 148, 1474-86 (1991).
57. Weinberger, D. R., Berman, K. F. & Chase, T. N. Mesocortical dopaminergic function and human cognition. Ann N Y Acad Sci 537, 330-8 (1988).
58. Laruelle, M., Kegeles, L. S. & Abi-Dargham, A. Glutamate, dopamine, and schizophrenia: from pathophysiology to treatment. Ann N Y Acad Sci 1003, 138-58 (2003).
59. Knable, M. B. & Weinberger, D. R. Dopamine, the prefrontal cortex and schizophrenia. J Psychopharmacol 11, 123-31 (1997).
60. Hall, H. et al. Distribution of D1- and D2-dopamine receptors, and dopamine and its metabolites in the human brain. Neuropsychopharmacology 11, 245-56 (1994).
61. Lidow, M. S., Goldman-Rakic, P. S., Gallager, D. W. & Rakic, P. Distribution of dopaminergic receptors in the primate cerebral cortex: quantitative autoradiographic analysis using [3H]raclopride, [3H]spiperone and [3H]SCH23390. Neuroscience 40, 657-71 (1991).
62. Okubo, Y. et al. Decreased prefrontal dopamine D1 receptors in schizophrenia revealed by PET. Nature 385, 634-6 (1997).

63. Abi-Dargham, A. et al. Prefrontal dopamine D1 receptors and working memory in schizophrenia. J Neurosci 22, 3708-19 (2002).
64. Williams, G. V. & Goldman-Rakic, P. S. Modulation of memory fields by dopamine D1 receptors in prefrontal cortex. Nature 376, 572-5 (1995).
65. Goldman-Rakic, P. S., Muly, E. C., 3rd & Williams, G. V. D (1) receptors in prefrontal cells and circuits. Brain Res Brain Res Rev 31, 295-301 (2000).
66. Castner, S. A., Williams, G. V. & Goldman-Rakic, P. S. Reversal of antipsychotic-induced working memory deficits by short-term dopamine D1 receptor stimulation. Science 287, 2020-2 (2000).
67. Davidson, M. et al. Effects of the D-1 agonist SKF-38393 combined with haloperidol in schizophrenic patients. Arch Gen Psychiatry 47, 190-1 (1990).
68. Muller, U., von Cramon, D. Y. & Pollmann, S. D1—versus D2-receptor modulation of visuospatial working memory in humans. J Neurosci 18, 2720-8 (1998).
69. Seeman, P., Niznik, H. B., Guan, H. C., Booth, G. & Ulpian, C. Link between D1 and D2 dopamine receptors is reduced in schizophrenia and Huntington diseased brain. Proc Natl Acad Sci USA 86, 10156-60. [1989].
70. Calabresi, P., R. Maj, N. B. Mercuri, and G. Bernardi, (1992) *Coactivation of D1 and D2 dopamine receptors is required for long-term synaptic depression in the striatum.* Neurosci Lett. 142(1): 95-9.
71. Castellano, C., S. Cabib, A. Palmisano, V. Di Marzo, and S. Puglisi-Allegra, (1997) *The effects of anandamide on memory consolidation in mice involve both D1 and D2 dopamine receptors.* Behav Pharmacol. 8(8): 707-12.
72. Gerfen, C. R., K. A. Keefe, and E. B. Gauda, (1995) *D1 and D2 dopamine receptor function in the striatum: coactivation of D1- and D2-dopamine receptors on separate populations of neurons results in potentiated immediate early gene response in D1-containing neurons.* J. Neurosci. 15(12): 8167-76.
73. Hyman, S. E., R. C. Malenka, and E. J. Nestler, (2006) *Neural mechanisms of addiction: the role of reward-related learning and memory.* Annu Rev Neurosci. 29: 565-98.
74. Keefe, K. A. and C. R. Gerfen, (1995) *D1-D2 dopamine receptor synergy in striatum: effects of intrastriatal infusions of dopamine agonists and antagonists on immediate early gene expression.* Neuroscience. 66(4): 903-13.
75. Sugahara, M. and H. Shiraishi, (1999) *Dopamine D1 and D2 receptor agents and their interaction influence the synaptic density of the rat prefrontal cortex.* Neurosci Lett. 259(3): 141-4.
76. Tang, Y. P., Y. Noda, and T. Nabeshima, (1997) *A synergistic interaction between dopamine D1 and D2 receptor subtypes in the memory impairments induced by concussive brain injury (CBI) in mice.* Behav Brain Res. 83(1-2): 189-93.
77. Lee, S. P., C. H. So, et al. (2004). "Dopamine D1 and D2 receptor Co-activation generates a novel phospholipase C-mediated calcium signal." J Biol Chem 279(34): 35671-8.
78. Rashid, A. J., C. H. So, M. M. Kong, et al., (2007) *D1-D2 dopamine receptor heterooligomers with unique pharmacology are coupled to rapid activation of Gq/11 in the striatum.* Proc Natl Acad Sci USA. 104(2): 654-9.
79. Surmeier D J, Reiner A, Levine M S, Ariano M A. Are neostriatal dopamine receptors co-localized? Trends Neurosci 16:299-305. (1993).
80. Vincent S L, Khan Y, Benes F M. Cellular colocalization of dopamine D1 and D2 receptors in rat medial prefrontal cortex. Synapse 19:112-120. (1995).
81. Missale, C., Nash, S. R., Robinson, S. W., Jaber, M., and Caron, M. G. (1998) Dopamine receptors: from structure to function. *Physiological reviews* 78, 189-225
82. Lee, F. J., S. Xue, L. Pei, et al., (2002) *Dual regulation of NMDA receptor functions by direct protein-protein interactions with the dopamine D1 receptor.* Cell. 111(2): 219-30.
83. Rashid, A. J., So, C. H., Kong, M. M., Furtak, T., El-Ghundi, M., Cheng, R., O'Dowd, B. F., and George, S. R. (2007) D1-D2 dopamine receptor heterooligomers with unique pharmacology are coupled to rapid activation of Gq/11 in the striatum. *Proceedings of the National Academy of Sciences of the United States of America* 104, 654-659
84. Lee, S. P., C. H. So, A. J. Rashid, et al., (2004) *Dopamine D1 and D2 receptor Co-activation generates a novel phospholipase C-mediated calcium signal.* J Biol Chem. 279 (34): 35671-8.
85. So, C. H., V. Verma, B. F. O'Dowd, and S. R. George, (2007) *Desensitization of the dopamine D1 and D2 receptor hetero-oligomer mediated calcium signal by agonist occupancy of either receptor.* Mol Pharmacol. 72(2): 450-62.
86. Edwards, E., Johnson, J., Anderson, D., Turano, P., and Henn, F. A. (1986) Neurochemical and behavioral consequences of mild, uncontrollable shock: effects of PCPA. *Pharmacol Biochem Behav* 25, 415-421
87. Setnik, B., de Souza, F. G., d'Almeida, V., and Nobrega, J. N. (2004) Increased homocysteine levels associated with sex and stress in the learned helplessness model of depression. *Pharmacol Biochem Behav* 77, 155-161
88. D'Aquila, P., Monleon, S., Borsini, F., Brain, P., and Willner, P. (1997) Anti-anhedonic actions of the novel serotonergic agent flibanserin, a potential rapidly-acting antidepressant. *Eur J Pharmacol* 340, 121-132
89. Kapur, S., VanderSpek, S. C., Brownlee, B. A., and Nobrega, J. N. (2003). Antipsychotic dosing in preclinical models is often unrepresentative of the clinical condition: a suggested solution based on in vivo occupancy. J Pharmacol Exp Ther 305, 625-631
90. Detke, M. J., Wieland, S., and Lucki, I. (1995) Blockade of the antidepressant-like effects of 8-OH-DPAT, buspirone and desipramine in the rat forced swim test by 5HT1A receptor antagonists. *Psychopharmacology (Berl)* 119, 47-54

What is claimed is:

1. A polypeptide of 15 or 17 to 100 amino acids in length, comprising an amino acid sequence that is 93% to 100% identical to the sequence of D2L$_{IL3\text{-}29\text{-}2}$ (SEQ ID NO:2).

2. The polypeptide of claim 1, consisting of D2L$_{IL3\text{-}29\text{-}2}$ (SEQ ID NO:2).

3. The polypeptide of claim 1, further comprising a protein transduction domain.

4. The polypeptide of claim 3, wherein the protein transduction domain is selected from the group consisting of Trans-Activator of Transcription (TAT), and SynB1/3Cit.

5. A method of modulating dopamine (DA) receptor function in a mammal, the method comprising:

administering to the mammal a polypeptide of 15 or 17 to 100 amino acids in length, the polypeptide including an amino acid sequence that is 93% to 100% identical to the sequence of D2L$_{IL3\text{-}29\text{-}2}$ (SEQ ID NO: 2).

6. The method of claim 5, wherein the polypeptide as administered consists of D2L$_{IL3\text{-}29\text{-}2}$ (SEQ ID NO:2).

7. The method of claim 5, wherein the polypeptide as administered further includes a protein transduction domain.

8. The method of claim 5, wherein the polypeptide as administered further includes a protein transduction domain selected from the group consisting of TAT and SynB1/3Cit.

* * * * *

SEQUENCE LISTING

<160> NUMBER OF SEQ ID NOS: 8

<210> SEQ ID NO 1
<211> LENGTH: 29
<212> TYPE: PRT
<213> ORGANISM: Homo Sapiens

<400> SEQUENCE: 1

Gly Asn Cys Thr His Pro Glu Asp Met Lys Leu Cys Thr Val Ile Met
1               5                   10                  15

Lys Ser Asn Gly Ser Phe Pro Val Asn Arg Arg Arg Val
            20                  25

<210> SEQ ID NO 2
<211> LENGTH: 15
<212> TYPE: PRT
<213> ORGANISM: Homo Sapiens

<400> SEQUENCE: 2

Ile Met Lys Ser Asn Gly Ser Phe Pro Val Asn Arg Arg Arg Val
1               5                   10                  15

<210> SEQ ID NO 3
<211> LENGTH: 163
<212> TYPE: PRT
<213> ORGANISM: Homo Sapiens

<400> SEQUENCE: 3

Lys Ile Tyr Ile Val Leu Arg Arg Arg Lys Arg Val Asn Thr Lys
1               5                   10                  15

Arg Ser Ser Arg Ala Phe Arg Ala His Leu Arg Ala Pro Leu Lys Gly
            20                  25                  30

Asn Cys Thr His Pro Glu Asp Met Lys Leu Cys Thr Val Ile Met Lys
        35                  40                  45

Ser Asn Gly Ser Phe Pro Val Asn Arg Arg Arg Val Glu Ala Ala Arg
50                  55                  60

Arg Ala Gln Glu Leu Glu Met Glu Met Leu Ser Ser Thr Ser Pro Pro
65                  70                  75                  80

Glu Arg Thr Arg Tyr Ser Pro Ile Pro Pro Ser His His Gln Leu Thr
                85                  90                  95

Leu Pro Asp Pro Ser His His Gly Leu His Ser Thr Pro Asp Ser Pro
            100                 105                 110

Ala Lys Pro Glu Lys Asn Gly His Ala Lys Asp His Pro Lys Ile Ala
        115                 120                 125

Lys Ile Phe Glu Ile Gln Thr Met Pro Asn Gly Lys Thr Arg Thr Ser
    130                 135                 140

Leu Lys Thr Met Ser Arg Arg Lys Leu Ser Gln Gln Lys Glu Lys Lys
145                 150                 155                 160

Ala Thr Gln

<210> SEQ ID NO 4
<211> LENGTH: 115
<212> TYPE: PRT
<213> ORGANISM: Homo Sapiens

<400> SEQUENCE: 4

Ala Phe Asn Ala Asp Phe Arg Lys Ala Phe Ser Thr Leu Leu Gly Cys
1               5                   10                  15

Tyr Arg Leu Cys Pro Ala Thr Asn Asn Ala Ile Glu Thr Val Ser Ile
            20                  25                  30

Asn Asn Asn Gly Ala Ala Met Phe Ser Ser His Glu Pro Arg Gly
        35                  40                  45

Ser Ile Ser Lys Glu Cys Asn Leu Val Tyr Leu Ile Pro His Ala Val
50                  55                  60

Gly Ser Ser Glu Asp Leu Lys Lys Glu Glu Ala Ala Gly Ile Ala Arg

```
                65                  70                  75                  80
Pro Leu Glu Lys Leu Ser Pro Ala Leu Ser Val Ile Leu Asp Tyr Asp
                        85                  90                  95

Thr Asp Val Ser Leu Glu Lys Ile Gln Pro Ile Thr Gln Asn Gly Gln
                    100                 105                 110

His Pro Thr
        115

<210> SEQ ID NO 5
<211> LENGTH: 443
<212> TYPE: PRT
<213> ORGANISM: Homo Sapiens

<400> SEQUENCE: 5

Met Asp Pro Leu Asn Leu Ser Trp Tyr Asp Asp Leu Glu Arg Gln
1               5                   10                  15

Asn Trp Ser Arg Pro Phe Asn Gly Ser Asp Gly Lys Ala Asp Arg Pro
                20                  25                  30

His Tyr Asn Tyr Tyr Ala Thr Leu Leu Thr Leu Leu Ile Ala Val Ile
            35                  40                  45

Val Phe Gly Asn Val Leu Val Cys Met Ala Val Ser Arg Glu Lys Ala
        50                  55                  60

Leu Gln Thr Thr Thr Asn Tyr Leu Ile Val Ser Leu Ala Val Ala Asp
65                  70                  75                  80

Leu Leu Val Ala Thr Leu Val Met Pro Trp Val Val Tyr Leu Glu Val
                85                  90                  95

Val Gly Glu Trp Lys Phe Ser Arg Ile His Cys Asp Ile Phe Val Thr
                100                 105                 110

Leu Asp Val Met Met Cys Thr Ala Ser Ile Leu Asn Leu Cys Ala Ile
            115                 120                 125

Ser Ile Asp Arg Tyr Thr Ala Val Ala Met Pro Met Leu Tyr Asn Thr
        130                 135                 140

Arg Tyr Ser Ser Lys Arg Arg Val Thr Val Met Ile Ser Ile Val Trp
145                 150                 155                 160

Val Leu Ser Phe Thr Ile Ser Cys Pro Leu Leu Phe Gly Leu Asn Asn
                165                 170                 175

Ala Asp Gln Asn Glu Cys Ile Ile Ala Asn Pro Ala Phe Val Val Tyr
            180                 185                 190

Ser Ser Ile Val Ser Phe Tyr Val Pro Phe Ile Val Thr Leu Leu Val
        195                 200                 205

Tyr Ile Lys Ile Tyr Ile Val Leu Arg Arg Arg Arg Lys Arg Val Asn
    210                 215                 220

Thr Lys Arg Ser Ser Arg Ala Phe Arg Ala His Leu Arg Ala Pro Leu
225                 230                 235                 240

Lys Gly Asn Cys Thr His Pro Glu Asp Met Lys Leu Cys Thr Val Ile
                245                 250                 255

Met Lys Ser Asn Gly Ser Phe Pro Val Asn Arg Arg Arg Val Glu Ala
            260                 265                 270

Ala Arg Arg Ala Gln Glu Leu Glu Met Glu Met Leu Ser Ser Thr Ser
        275                 280                 285

Pro Pro Glu Arg Thr Arg Tyr Ser Pro Ile Pro Ser His His Gln
    290                 295                 300

Leu Thr Leu Pro Asp Pro Ser His His Gly Leu His Ser Thr Pro Asp
305                 310                 315                 320

Ser Pro Ala Lys Pro Glu Lys Asn Gly His Ala Lys Asp His Pro Lys
```

```
                    325                 330                 335
Ile Ala Lys Ile Phe Glu Ile Gln Thr Met Pro Asn Gly Lys Thr Arg
            340                 345                 350
Thr Ser Leu Lys Thr Met Ser Arg Arg Lys Leu Ser Gln Gln Lys Glu
            355                 360                 365
Lys Lys Ala Thr Gln Met Leu Ala Ile Val Leu Gly Val Phe Ile Ile
            370                 375                 380
Cys Trp Leu Pro Phe Phe Ile Thr His Ile Leu Asn Ile His Cys Asp
385                 390                 395                 400
Cys Asn Ile Pro Pro Val Leu Tyr Ser Ala Phe Thr Trp Leu Gly Tyr
            405                 410                 415
Val Asn Ser Ala Val Asn Pro Ile Ile Tyr Thr Thr Phe Asn Ile Glu
            420                 425                 430
Phe Arg Lys Ala Phe Leu Lys Ile Leu His Cys
            435                 440
```

<210> SEQ ID NO 6
<211> LENGTH: 1332
<212> TYPE: DNA
<213> ORGANISM: Homo Sapiens

<400> SEQUENCE: 6

```
atggatccac tgaatctgtc ctggtatgat gatgatctgg agaggcagaa ctggagccgg      60
cccttcaacg ggtcagacgg gaaggcggac agaccccact acaactacta tgccacactg     120
ctcaccctgc tcatcgctgt catcgtcttc ggcaacgtgc tggtgtgcat ggctgtgtcc     180
cgcgagaagg cgctgcagac caccaccaac tacctgatcg tcagcctcgc agtggccgac     240
ctcctcgtcg ccacactggt catgcccctgg gttgtctacc tggaggtggt aggtgagtgg     300
aaattcagca ggattcactg tgacatcttc gtcactctgg acgtcatgat gtgcacggcg     360
agcatcctga acttgtgtgc catcagcatc gacaggtaca cagctgtggc catgcccatg     420
ctgtacaata cgcgctacag ctccaagcgc cgggtcaccg tcatgatctc catcgtctgg     480
gtcctgtcct tcaccatctc ctgcccactc tcttcggac tcaataacgc agaccagaac     540
gagtgcatca ttgccaaccc ggccttcgtg gtctactcct ccatcgtctc cttctacgtg     600
cccttcattg tcaccctgct ggtctacatc aagatctaca ttgtcctccg cagacgccgc     660
aagcgagtca acaccaaacg cagcagccga gctttcaggg cccacctgag ggctccacta     720
aagggcaact gtactcaccc cgaggacatg aaactctgca ccgttatcat gaagtctaat     780
gggagtttcc cagtgaacag gcggagagtg gaggctgccc ggcgagccca ggagctggag     840
atggagatgc tctccagcac cagcccaccc gagaggaccc ggtacagccc catcccaccc     900
agccaccacc agctgactct ccccgacccg tccaccatg gtctccacag cactcccgac     960
agccccgcca aaccagagaa gaatgggcat gccaaagacc accccaagat tgccaagatc    1020
tttgagatcc agaccatgcc caatggcaaa acccggacct ccctcaagac catgagccgt    1080
aggaagctct cccagcagaa ggagaagaaa gccactcaga tgctcgccat tgttctcggc    1140
gtgttcatca tctgctggct gcccttcttc atcacacaca tcctgaacat acactgtgac    1200
tgcaacatcc cgcctgtcct gtacagcgcc ttcacgtggc tgggctatgt caacagcgcc    1260
gtgaacccca tcatctacac cacctttcaac attgagttcc gcaaggcctt cctgaagatc    1320
ctccactgct ga                                                        1332
```

<210> SEQ ID NO 7
<211> LENGTH: 446

<212> TYPE: PRT
<213> ORGANISM: Homo Sapiens

<400> SEQUENCE: 7

```
Met Arg Thr Leu Asn Thr Ser Ala Met Asp Gly Thr Gly Leu Val Val
1               5                   10                  15

Glu Arg Asp Phe Ser Val Arg Ile Leu Thr Ala Cys Phe Leu Ser Leu
            20                  25                  30

Leu Ile Leu Ser Thr Leu Leu Gly Asn Thr Leu Val Cys Ala Ala Val
        35                  40                  45

Ile Arg Phe Arg His Leu Arg Ser Lys Val Thr Asn Phe Phe Val Ile
    50                  55                  60

Ser Leu Ala Val Ser Asp Leu Leu Val Ala Val Leu Val Met Pro Trp
65                  70                  75                  80

Lys Ala Val Ala Glu Ile Ala Gly Phe Trp Pro Phe Gly Ser Phe Cys
                85                  90                  95

Asn Ile Trp Val Ala Phe Asp Ile Met Cys Ser Thr Ala Ser Ile Leu
            100                 105                 110

Asn Leu Cys Val Ile Ser Val Asp Arg Tyr Trp Ala Ile Ser Ser Pro
        115                 120                 125

Phe Arg Tyr Glu Arg Lys Met Thr Pro Lys Ala Ala Phe Ile Leu Ile
130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
            180                 185                 190

Thr Tyr Ala Ile Ser Ser Ser Val Ile Ser Phe Tyr Ile Pro Val Ala
        195                 200                 205

Ile Met Ile Val Thr Tyr Thr Arg Ile Tyr Arg Ile Ala Gln Lys Gln
210                 215                 220

Ile Arg Arg Ile Ala Ala Leu Glu Arg Ala Ala Val His Ala Lys Asn
225                 230                 235                 240

Cys Gln Thr Thr Thr Gly Asn Gly Lys Pro Val Glu Cys Ser Gln Pro
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Leu Asn Cys Ile Leu Pro Phe Cys Gly Ser Gly Glu Thr Gln
290                 295                 300

Pro Phe Cys Ile Asp Ser Asn Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Arg Lys Ala Phe Ser Thr Leu Leu Gly Cys Tyr Arg Leu Cys Pro
            340                 345                 350

Ala Thr Asn Asn Ala Ile Glu Thr Val Ser Ile Asn Asn Asn Gly Ala
        355                 360                 365

Ala Met Phe Ser Ser His His Glu Pro Arg Gly Ser Ile Ser Lys Glu
370                 375                 380

Cys Asn Leu Val Tyr Leu Ile Pro His Ala Val Gly Ser Ser Glu Asp
385                 390                 395                 400
```

-continued

```
Leu Lys Lys Glu Glu Ala Ala Gly Ile Ala Arg Pro Leu Glu Lys Leu
            405                 410                 415

Ser Pro Ala Leu Ser Val Ile Leu Asp Tyr Asp Thr Asp Val Ser Leu
            420                 425                 430

Glu Lys Ile Gln Pro Ile Thr Gln Asn Gly Gln His Pro Thr
            435                 440                 445

<210> SEQ ID NO 8
<211> LENGTH: 1341
<212> TYPE: DNA
<213> ORGANISM: Homo Sapiens

<400> SEQUENCE: 8
atgaggactc tgaacacctc tgccatggac gggactgggc tggtggtgga gagggacttc      60
tctgttcgta tcctcactgc ctgtttcctg tcgctgctca tcctgtccac gctcctgggg     120
aacacgctgg tctgtgctgc cgttatcagg ttccgacacc tgcggtccaa ggtgaccaac     180
ttctttgtca tctccttggc tgtgtcagat ctcttggtgg ccgtcctggt catgccctgg     240
aaggcagtgg ctgagattgc tggcttctgg cccttgggt ccttctgtaa catctgggtg      300
gcctttgaca tcatgtgctc cactgcatcc atcctcaacc tctgtgtgat cagcgtggac     360
aggtattggg ctatctccag ccctttccgg tatgagagaa agatgacccc caaggcagcc     420
ttcatcctga tcagtgtggc atggaccttg tctgtactca tctccttcat cccagtgcag     480
ctcagctggc acaaggcaaa acccacaagc ccctctgatg gaaatgccac ttccctggct     540
gagaccatag acaactgtga ctccagcctc agcaggacat atgccatctc atcctctgta     600
ataagctttt acatccctgt ggccatcatg attgtcacct acaccaggat ctacaggatt     660
gctcagaaac aaatacggcg cattgcggcc ttggagaggg cagcagtcca cgccaagaat     720
tgccagacca ccacaggtaa tggaaagcct gtcgaatgtt ctcaaccgga aagttctttt     780
aagatgtcct tcaaaagaga aactaaagtc ctgaagactc tgtcggtgat catgggtgtg     840
tttgtgtgct gttggctacc tttcttcatc ttgaactgca ttttgccctt ctgtgggtct     900
ggggagacgc agccccttctg cattgattcc aacacctttg acgtgtttgt gtggtttggg     960
tgggctaatt catccttgaa ccccatcatt tatgccttta atgctgattt tcggaaggca    1020
ttttcaaccc tcttaggatg ctacagactt tgccctgcga cgaataatgc catagagacg    1080
gtgagtatca ataacaatgg ggccgcgatg ttttccagcc atcatgagcc acgaggctcc    1140
atctccaagg agtgcaatct ggtttacctg atcccacatg ctgtgggctc ctctgaggac    1200
ctgaaaaagg aggaggcagc tggcatcgcc agacccttgg agaagctgtc cccagcccta    1260
tcagtcatat tggactatga cactgacgtc tctctggaga agatccaacc catcacacaa    1320
aacggtcagc acccaacctg a                                              1341
```